United States Patent
Pecorari et al.

(10) Patent No.: US 11,434,585 B2
(45) Date of Patent: *Sep. 6, 2022

(54) OB-FOLD USED AS SCAFFOLD FOR ENGINEERING NEW SPECIFIC BINDERS

(71) Applicants: INSTITUT PASTEUR, Paris (FR); CENTRE NATIONAL DE LA RECHERCHE SCIENTIFIQUE, Paris (FR)

(72) Inventors: Frédéric Pecorari, Nantes (FR); Pedro Alzari, Paris (FR)

(73) Assignees: INSTITUT PASTEUR, Paris (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 126 days.

This patent is subject to a terminal disclaimer.

(21) Appl. No.: 16/752,140

(22) Filed: Jan. 24, 2020

(65) Prior Publication Data

US 2020/0181601 A1    Jun. 11, 2020

Related U.S. Application Data

(63) Continuation of application No. 15/266,676, filed on Sep. 15, 2016, now Pat. No. 10,584,330, which is a (Continued)

(30) Foreign Application Priority Data

Dec. 4, 2006  (EP) .................................... 06291869

(51) Int. Cl.
    *C40B 40/10*    (2006.01)
    *C07K 14/195*    (2006.01)
    (Continued)

(52) U.S. Cl.
    CPC ............ *C40B 40/10* (2013.01); *C07K 14/195* (2013.01); *C07K 16/1228* (2013.01);
    (Continued)

(58) Field of Classification Search
    None
    See application file for complete search history.

(56) References Cited

U.S. PATENT DOCUMENTS 5,942,387 A    8/1999  Hollinshead
6,696,248 B1   2/2004  Knappik et al.
(Continued)

FOREIGN PATENT DOCUMENTS

WO   WO-2002/32925 A2    4/2002
WO   WO-2006/013468 A2   2/2006
WO   WO-2007/139397 A1  12/2007

OTHER PUBLICATIONS

Peters, W.B. et al., "Effect of Mutation of the Sac7d Intercalating Residues on the Temperature Dependence of DNA Distortion and Binding Thermodynamics", Biochemistry, vol. 44, No. 12, pp. 4794-4804 (2005).

(Continued)

*Primary Examiner* — Christian C Boesen
(74) *Attorney, Agent, or Firm* — Polsinelli PC

(57) ABSTRACT

The present invention pertains to the field of protein engineering, and provides means for obtaining stable molecules that specifically bind to a target selected amongst a large variety of ligands families. In particular, the present invention provides methods for obtaining a molecule specifically binding to a target of interest, through a combinatorial mutation/selection approach with an OB-fold protein as a starting molecule. In particular, the target of interest can be (Continued)

of a different chemical nature form that of the native target of the OB-fold protein used as the starting molecule.

20 Claims, 16 Drawing Sheets

Specification includes a Sequence Listing.

Related U.S. Application Data continuation of application No. 12/517,643, filed as application No. PCT/IB2007/004388 on Dec. 4, 2007, now abandoned.

(51) Int. Cl.
*C07K 16/12* (2006.01)
*C07K 16/42* (2006.01)
*C12N 15/10* (2006.01)
*C40B 30/04* (2006.01)

(52) U.S. Cl.
CPC ...... *C07K 16/1232* (2013.01); *C07K 16/4283* (2013.01); *C12N 15/1041* (2013.01); *C07K 2318/20* (2013.01); *C40B 30/04* (2013.01)

(56) References Cited

U.S. PATENT DOCUMENTS

| | | |
|---|---|---|
| 7,462,490 B2 | 12/2008 | Wollenberg et al. |
| 7,659,100 B2 | 2/2010 | Borns |
| 2004/0219558 A1 | 11/2004 | Vander Horn et al. |
| 2008/0103055 A1 | 5/2008 | Kristensen |
| 2010/0279360 A1 | 11/2010 | Wang |

OTHER PUBLICATIONS

Mou, T-C. et al., "binding and Reversible Deunaturation of Double-Stranded DNA by Ff Gene 5 Protein", Biopolymers, vol. 70, No. 4, pp. 637-648 (2003).
Binz, H. K. et al., "Engineering Novel Binding Proteins From Nonimmunoglobulin Domains", Nature Biotechnology, vol. 23, No. 10, pp. 1257-1268 (2005).
Gao, Y.-G. et al., "The Crystal Structure of the Hyperthermophyle Chromosomal Protein SsO7d Bound to DNA, Nature Structural Biology", vol. 5, No. 9, pp. 782-786 (1998).
Arcus, V., "OB-Fold Domains: A Snapshot of the Evolution of Sequence, Structure and Function", Current Opinion in Structural Biology, vol. 12, No. 6, pp. 794-801 (2002).
Drevelle, A. et al., "Structures of In Vitro Evolved binding Sites on Neocarzinostatin Scaffold Reveal Unanticipated Evolutionary Pathways", Journal of Molecular Biology, vol. 358, No. 2, pp. 455-471 (2006).
Mirny, L.A. et al., "Universally Conserved Positions in Protein Folds:Reading Evolutionary Signals About Stability, Folding Kinetics and Function", Journal of Molecular Biology, vol. 291, No. 1 pp. 177-196 (1999).
McAfee, et al., Biochemistry, vol. 34, pp. 10063-10077 (1995).
Norman, T.C. et al., "Genetic selection of peptide inhibitors of biological pathways", Science, American Association for the Advancement of Science, vol. 285, No. 5427, pp. 591-595 (1999).
Dualsystems Biotech AG Protein InteraCtion Kits Information ( 4 pages) (2011).
Dualsystems Biotech Price List 2011 (10 pages) (2011).
Clontech Laboratories, Inc., Product information on Just Mate and Plate TM yeast two-hybrid library screening product. ( 1 page) 2011.
New England BioLabs Inc. Product information for Ph.D. I M Phage Display Peptide Library (3 pages) (2011).
New England BioLabs Inc., Ph.D. Phage Display Libraries Instruction Manual ( 44 pages) (2011).
Robinson, H. et al., "The hyperthermophile chromosomal protein Sac7d sharply kinks DNA", Nature, vol. 392, pp. 202-205 (1998).
Agback, P., "Architecture of nonspecific protein-DNA interactions in the Sso7d-DNA complex", Nature Structural Biology, vol. 5, No. 7, pp. 579-584 (1998).

Sso7d            Superomposition with Sac7d

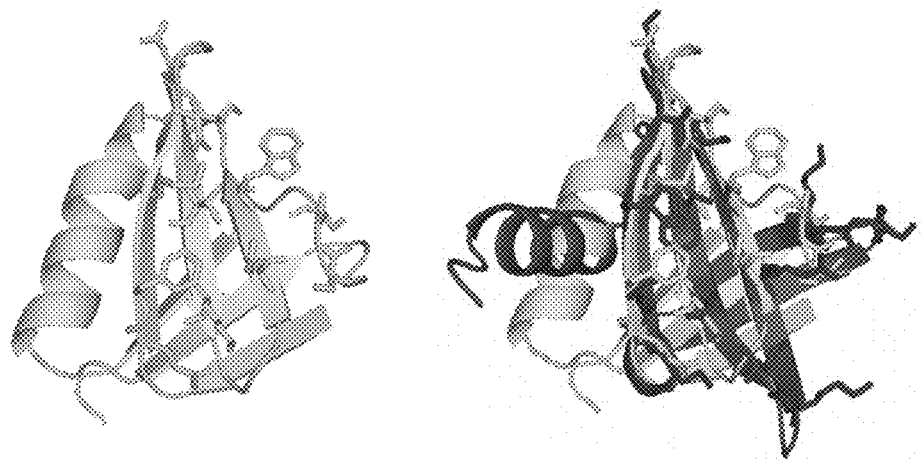
Shiga-like toxin IIe  Superimposition with Sac7d
FIG. 3b
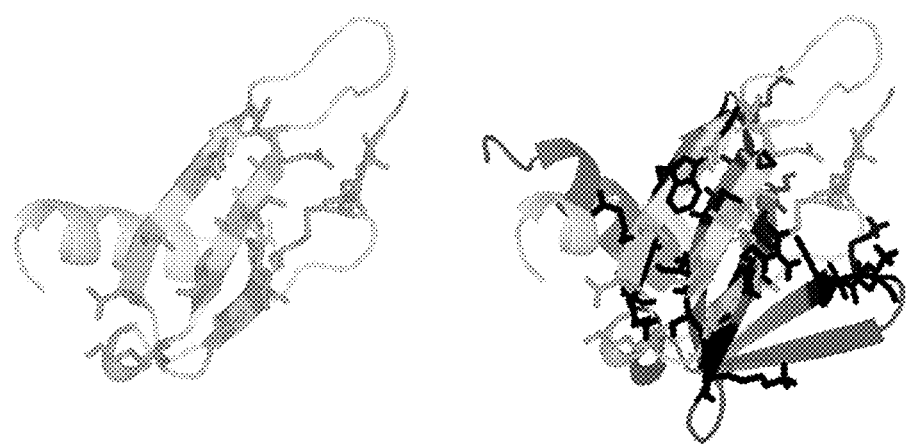
NAP-2  Superimposition with Sac7d
FI

```
Sac7d    VKVKFKYKGEEKEVDTSKIKKVWRVGKMVSFTYDDNGKTGRGAVSEKDAPKELLDMLARAERE-KK
Sac7e    -..R.........................................M.......K--..
DBP  7   .T..........I........I........................Q..---.KSG..
Ssh7b    .T..........I.....EG..........................Q..---.KQ-..
Sso7d    --..........I........I.....EG.................Q..---.KQ-..
Ssh7a    --........Q..I........I.....EG.................Q..---.KQ-..
```
Figure 4
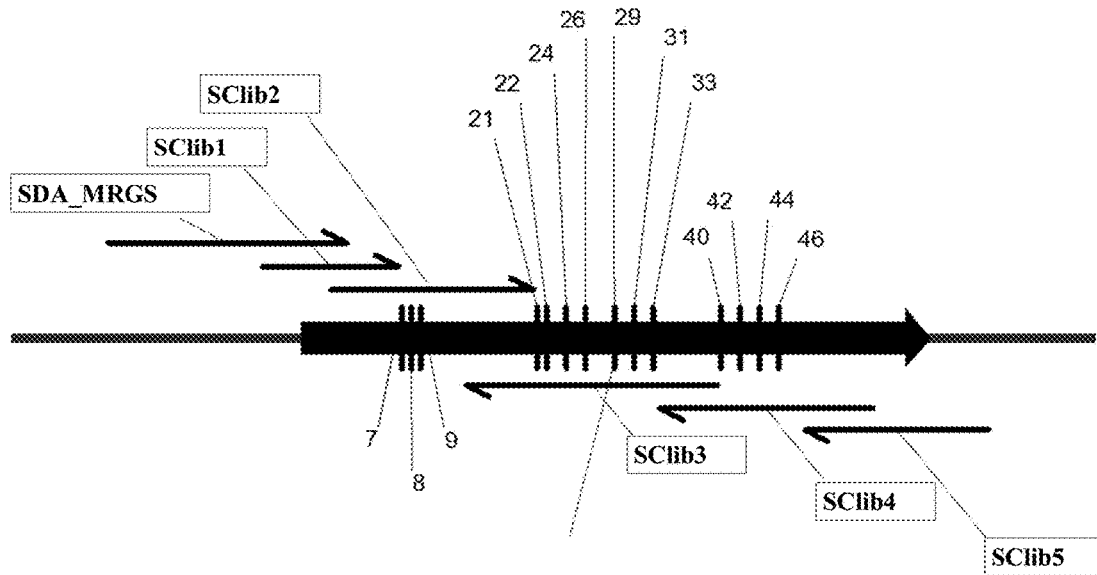
Fig. 5
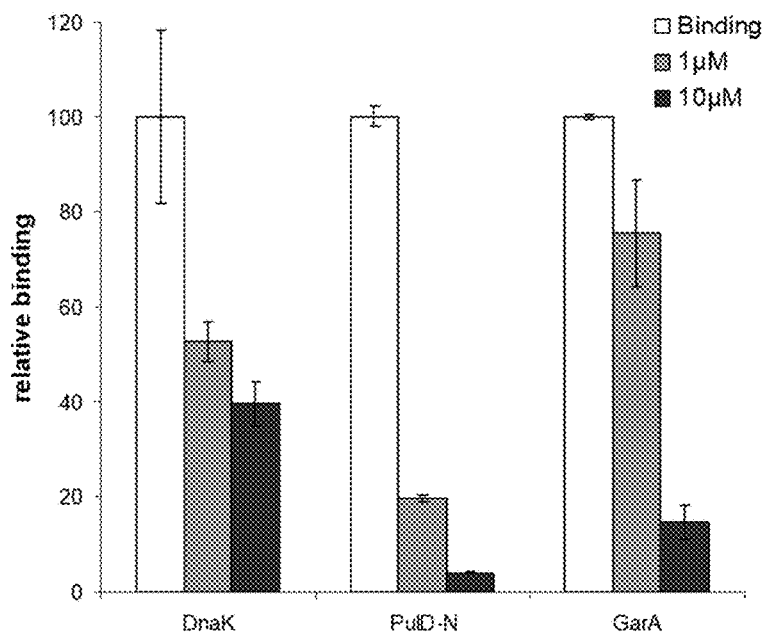
Fig. 6a

FIG. 8

```
              10        20        30        40        50        60
              |         |         |         |         |         |
Sac7d  VKVKFKYKGEEKEVDTSKIKKVWRVGKMVSFTYDDNGKTGRGAVSEKDAPKELLDMLARAEREKK
6      ....VLG............RH.Y...H.S........L.L.K.....................
19     ....MGS............RS.G...A.R........N.Y.D.....................
24     ....TVI............LR.A...C.R........H.Y.H.....................
33     ....TWY............MS.C...A.S......IDY.D.......................
39     ....CWE............RH.Y...T.S........L.L.N.................A...
40     ....GEH............MS.V...C.R........A.Y..H....................
41     ....VMS............MS.V...C.R........A.Y.H.....................
44     ....ETS............SS.A...A.R........M.V.P.....................
```

OB-FOLD USED AS SCAFFOLD FOR ENGINEERING NEW SPECIFIC BINDERS

CROSS REFERENCE TO RELATED APPLICATIONS

This application is a Continuation of U.S. application Ser. No. 15/266,676, filed Sep. 15, 2016. U.S. application Ser. No. 15/266,676 is a Continuation of U.S. application Ser. No. 12/517,643, filed Jul. 24, 2009. U.S. application Ser. No. 12/517,643 is a national stage application (under 35 U.S.C. § 371) of PCT/IB2007/004388, filed Dec. 4, 2007, which claims benefit of European application EP 06291869.3, filed Dec. 4, 2006; the entire contents of which is fully incorporated herein by reference.

SEQUENCE LISTING SUBMISSION VIA EFS-WEB

A computer readable text file, entitled "BRV50-US-CNT2-Sequence-Listing.txt", created on or about Jan. 23, 2020, with a file size of about 48000 bytes contains the sequence listing for this application and is hereby incorporated by reference in its entirety.

The present invention pertains to the field of protein engineering. More specifically, the invention provides means for obtaining stable molecules that specifically bind to a target selected amongst a large variety of ligands families.

Most natural proteins are not adapted to therapeutic or even biotechnological uses. The challenge of protein engineering is to define efficient and comprehensive ways for the design of new or improved proteins with the required properties. Among targeted properties, recognition of a ligand with high specificity and affinity is of premium importance. For many applications, antibodies have been used because of their extraordinary adaptability to binding very different kinds of ligands, such as proteins, peptides, nucleic acids, sugars, etc. However, antibodies or their derivative fragments are often difficult and expensive to produce because of their molecular complexity and/or their insufficient stability. For these reasons, alternatives to antibodies have recently been developed using scaffold proteins engineered via a combinatorial mutation/selection approach. The aim was to maintain favorable properties of antibodies, while getting rid of their disadvantages. Successful applications of this strategy have been reported (Binz et al., 2005; Mathonet and Fastrez, 2004), the vast majority of targets being proteins and, exceptionally, small organic compounds.

The present invention aims at providing tools for engineering molecules well adapted to medical or biotechnological uses, and able to bind specifically and with a high affinity to various targets, selected amongst nucleic acids, proteins, carbohydrates or any other biological molecule. To this aim, the inventors have tested the hypothesis that a particular protein structure, named oligonucleotide/oligosaccharide binding-fold (OB-fold), might be modified by randomization of the residues of its binding face, while at least partially maintaining the favorable biophysical properties of the parent protein (i.e., high stability and folding efficiency).

The oligonucleotide/oligosaccharide binding-fold (OB-fold), first described by Murzin (Murzin, 1993), is found in all kingdoms and was ranked as the 28th most represented fold in a survey of 20 genomes (Qian et al., 2001). This fold, a five stranded β-barrel capped with an amphiphilic α-helix, appears suitable for a wide diversity of sequences. The OB-fold presents a β-sheet binding face that confers remarkable diversity in the types of compounds that can be recognized: ssDNA, dsDNA, RNA, oligosaccharides, proteins, metallic ions and catalytic substrates. A study of several OB-folds from different proteins showed that the binding core is always located at the same position of the binding face (Arcus, 2002).

Sac7d has an OB-fold topology (FIG. 1a) (Agback et al., 1998; Gao et al., 1998; Robinson et al., 1998; Su et al., 2000). It belongs to a class of small chromosomal proteins from the hyperthermophilic archaeon *Sulfolobus acidocaldarius*. Sac7d binds double strand DNA without any particular sequence preference, while inducing a sharp kink in the DNA (Robinson et al., 1998). It is thought to play a role in DNA helix stabilization at the high growth temperature of *Sulfolobus acidocaldarius* (optimal at 85° C.). Sac7d is extremely stable. It is thermostable and unfolds with a $T_m$ of 91° C., it maintains a native fold between pH 0 and 10, and its guanidinium hydrochloride induced denaturation occurs reversibly with a midpoint concentration of 2.8 M denaturant (McCrary et al., 1996). Contrary to antibodies, its molecular organization is quite simple. Sac7d is a small monomeric protein of 66 amino acids, with one structural domain (i.e., the OB-fold), and does not have a disulfide bridge (McAfee et al., 1995). Several truncated forms of Sac7d have been observed (McAfee et al., 1995). Overproduction levels up to 10-15 mg of soluble protein per liter flask culture of *Escherichia coli* can be reached (Edmondson and Shriver, 2001). Structural studies of Sac7d and its close homologue Sso7d from *Sulfolobus solfataricus* have shown that the two protein cores are superimposable and that binding to the minor groove of DNA occurs mainly via a twisted area formed by 16 residues (Agback et al., 1998; Gao et al., 1998; Robinson et al., 1998).

The inventors have explored the possibility to change the binding specificity of Sac7d by in vitro directed protein evolution, through the introduction of random mutations in a number of residues involved in the ligand binding, followed by a selection of the variants which bind to a given target. More precisely, the inventors have constructed a large library of about $3·10^{12}$ variants corresponding to random substitutions of 11 residues of the binding interface of Sac7d. This library has been used to select variants able to bind a defined protein target, by ribosome display. Pools of binders for three protein targets were obtained, with affinities in the hundred nanomolars range. In a second approach, the inventors extended the potential binding area up to 13 and 14 residues. These new libraries were used for selection on one of the previous targets (PulD-N), and specific binders with affinity in the picomolar range were obtained. Hence, the inventors have demonstrated that, surprisingly, a general DNA binder (Sac7d) can be evolved towards a specific protein binder having high specificity and affinity. This demonstration provides a proof of principle that binders for virtually any kind of ligand can be derived from Sac7d or other OB-fold proteins, for example by using the process described in more detail below.

A first aspect of the present invention is hence the use of an OB-fold protein, as a starting molecule for obtaining, through a combinatorial mutation/selection approach, a molecule specifically binding to a target, especially to a target to which the starting OB-fold protein does not bind, i.e., to a target different form the target of the OB-fold protein used as the starting molecule. In what follows, the target of the starting OB-fold protein will be called the "native target", whereas the target used in the selection step will be designated as the "target of interest". In a preferred embodiment, the target of interest is of a chemical nature different from that of the native target (for examples, protein vs./nucleic acid, and metallic ion or sugar vs./protein). A particular aspect of the present invention is hence the use of an OB-fold protein naturally binding to a nucleic acid, as a starting molecule for obtaining, through a combinatorial mutation/selection approach, a molecule specifically binding to a target different from a nucleic acid (for example, a protein). The use of an OB-fold protein naturally binding to a protein, as a starting molecule for obtaining, through a combinatorial mutation/selection approach, a molecule specifically binding to a non-protein target (for example, a nucleic acid) is also part of the present invention.

According to the present invention, the phrase "OB-fold protein" designates any polypeptide which comprises or consists of a domain having OB-fold topology, as described by (Murzin, 1993) and (Arcus, 2002). This topology corresponds to an architecture which comprises a five-stranded β-barrel capped at one end by an amphiphilic α-helix. Referring to the CATH protein structure classification (Pearl et al., 2003), the OB-fold topology corresponds to the 2.40.50 fold family (CATH database version 3.0.0: Released May 2006). Such an OB-fold protein can be either a native protein (i.e., an isolated, purified or recombinant protein having the same sequence as a natural protein), or an engineered protein (like, for example, a fragment of a native protein, or a fusion protein comprising an OB-fold domain from a first protein, and another moiety from another protein). Non-limitative examples of OB-fold proteins which can be used according to the invention are Sac7d, Sso7d, the N-terminal domain of SEB (Papageorgiou et al., 1998), the chain A of the Shiga-like toxin IIe (PDB 2bosa), the human Neutrophil Activatin Peptide-2 (NAP-2, PDB 1tvxA), the Molybdenum Binding Protein (modg) of *Azotobacter vinelandii* (PDB 1h9j), the N-terminal domain of SPE-C (Roussel et al., 1997), the $B_5$ subunit of *E. coli* Shiga-like toxin (Kitov et al., 2000), Cdc13 (Mitton-Fry et al., 2002), the cold-shock DNA-binding domain of the human Y-box protein YB-1 (Kloks et al., 2002), the *E. coli* inorganic pyrophosphatase EPPase (Samygina et al., 2001), or any of the proteins listed in Table 3 of the article by (Arcus, 2002), such as 1krs (Lysyl-tRNA synthetase LysS, *E. coli*), 1c0aA (Asp-tRNA synthetase, *E. coli*), 1b8aA (Asp-tRNA synthetase, *P. kodakaraensis*), 1lylA (Lysyl-tRNA synthetase LysU, *E. coli*), 1quqA (Replication protein A, 32 kDa subunit, Human), 1quqB (Replication protein A, 14 kDa subunit, Human), 1jmcA (Replication protein A, 70 kDa subunit (RPA70) fragment, Human), 1otc (Telomere-end-binding protein, *O. nova*), 3ullA (Mitochondrial ssDNA-binding protein, Human), 1prtF (Pertussis toxin S5 subunit, *B. pertussis*), 1bcpD (Pertussis toxin S5 subunit (ATP bound), *B. pertussis*), 3chbD (Cholera Toxin, *V. cholerae*), 1tiiD (Heat-labile toxin, *E. coli*), 2bosA (Verotoxin-1/Shiga toxin, B-pentamer, *E. coli*), 1br9 (TIMP-2, Human), 1an8 (Superantigen SPE-C, *S. pyogenes*), 3seb (Superantigen SPE, *S. aureus*), 1aw7A (Toxic shock syndrome toxin, *S. aureus*), 1jmc (Major cold-shock protein, *E. coli*), 1bkb (Initiation translation factor 5a, *P. aerophylum*), 1sro (S1 RNA-binding domain of PNPase, *E. coli*), 1d7qA (Initiation translation factor 1, eIF1a, Human), 1ah9 (Initiation translation factor 1, IF1, *E. coli*), 1b9 mA (Mo-dependent transcriptional regulator ModE, *E. coli*), 1ckmA (RNA guanylyltransferase, *Chlorella* virus, PBCV-1), 1a0i (ATP-dependent DNA ligase, Bacteriophage T7), 1snc (*Staphylococcal nuclease, S. aureus*), 1hjp (DNA helicase RuvA subunit, N-terminal domain, *E. coli*), 1pfsA (Gene V protein, *Pseudomonas* bacteriophage pf3), 1gvp (Gene V protein, Filamentous bacteriophage (f1, M13)), 1gpc (Gene 32 protein (gp32) core, Bacteriophage T4), 1wgjA (Inorganic pyrophosphatase, *S. cerevisiae*), and 2prd (Inorganic pyrophosphatase, *T. thermophilus*). It can be noted that OB-folds domains originating from toxins can be used as starting molecules even for purposes in which toxicity is to be avoided, since mutations in their binding site, and hence change in their binding specificity, can completely abolish their toxicity.

As exemplified in more detail in the experimental part below, the combinatorial mutation/selection approach consists in obtaining a combinatorial library corresponding to the randomization of a number of chosen residues of the starting OB-fold protein (especially, randomization of a number of residues involved in the binding of the protein with its native ligand), followed by a selection, in said library, of variants which have the desired properties.

Another object of the present invention is hence a combinatorial library corresponding to the randomization of 5 to 32, preferably 8 to 20, and more preferably 11 to 16 residues of the binding interface of an OB-fold protein with its native ligand, possibly combined with the deletion of 1 to 4 residues and/or the insertion of 1 to 50 residues. Of course, the "binding interface of an OB-fold protein" herein designates, even in cases of proteins with multiple domains binding to different ligands, the interface between the OB-fold domain and the ligand which binds to this domain. The skilled artisan will find in the scientific literature the necessary information to identify the residues involved in the binding of the OB-fold protein with its native ligand, which are often located in β-strands β3, β4 and β5 and in loops 1, 3 and 4 of the OB-fold (FIGS. 1b and 2).

Particular combinatorial libraries according to the present invention can be obtained with Sac7d from *Sulfolobus acidocaldarius*, or with its homologues (FIG. 4) such as Sso7d Sso7d from *Sulfolobus solfataricus*. Of course, libraries obtained with a truncated form of Sac7d, such as those described by (McAfee et al., 1995), are also part of the present invention.

By superimposing several sequences and 3D-structures of OB-fold domains using the web sites WU-Blast2 (www.ebi.ac.uk/blast2/index.html) (Lopez et al., 2003), T-COFFEE (www.ch.embnet.org/software/TCoffee.html) (Notredame et al., 2000) and DALI lite (www.ebi.ac.uk/DaliLite/) (Holm and Park, 2000), the inventors have identified the positions which could be modified for obtaining the libraries according to the present invention. Taking as a reference the sequence of Sac7d of SEQ ID No: 1, the residues which can be randomized are the following: V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51.

Still with Sac7d as a reference, the residues which can be deleted are: A59, R60, A61 and E64.

A superimposition of 3D structures of 10 proteins or OB-fold domains (including Sac7d), using the web site DALI (www.ebi.ac.uk/dali/Interactive.html) (Holm and Sander, 1998), revealed that this kind of proteins have loops of various sizes, which most probably are involved in the binding of ligands (see FIG. 2). This observation is consistent with previously published data (Arcus, 2002). Since Sac7d is one of the proteins having the shortest loops, random insertions in said loops can advantageously be performed in order to obtain libraries particularly adapted for the binding of certain ligands families. Advantageously, insertions of 1 to 15 amino acid residues can be performed in loop 3 (as identified in FIGS. 1b and 2), for example in the region of residues 25 to 30 of Sac7d, preferably between residues 27 and 28, insertions of 1 to 15 amino acid residues can be performed in loop 4 (as identified in FIGS. 1b and 2), for example in the region of residues 35 to 40 of Sac7d, preferably between residues 37 and 38, and insertions of 1 to 20 amino acid residues can be performed in loop 1 (as identified in FIGS. 1b and 2), for example in the region of residues 7 to 12 of Sac7d, preferably between residues 9 and 10. In order to avoid any ambiguity, it is herein specified that loops 3, 4 and 1 as identified in FIGS. 1a and 2 respectively correspond to loops 1, 2 and 4 identified in the review article by. Arcus (supra).

According to a particular embodiment of the invention, the combinatorial library corresponds to the randomization of 11, 12, 13, 14, 15, 16, 17 or 18 residues of Sac7d selected amongst K7, Y8, K9, K21, K22, W24, V26, K28, M29, S31, T33, K39, T40, R42, A44, S46, E47 and K48, for example 11, 12, 13, 14, 15 or 16 residues selected amongst K7, Y8, K9, K21, K22, W24, V26, K28, M29, S31, T33, K39, T40, R42, A44 and S46.

In a preferred combinatorial library of the above embodiment, the randomized residues comprise at least the residues K7, Y8, K9, W24, V26, M29, S31, T33, R42, A44 and S46 of Sac7d. A specific library according to this embodiment, and designated in the experimental part below as "library 11", corresponds to the randomization of the residues K7, Y8, K9, W24, V26, M29, S31, T33, R42, A44 and S46 of Sac7d. In other combinatorial libraries according to this embodiment, one, two or three additional residues of Sac7d selected amongst K21, K22 and T40 are also randomized Two other preferred libraries according to the invention, also described in the experimental part, are "library 13", which corresponds to the randomization of the residues K7, Y8, K9, K21, K22, W24, V26, M29, S31, T33, R42, A44 and S46 of Sac7d, and "library 14", which corresponds to the randomization of the residues K7, Y8, K9, K21, K22, W24, V26, M29, S31, T33, T40, R42, A44 and S46 of Sac7d.

Of course, a combinatorial library obtained by randomizing 11, 12, 13, 14, 15 or 16 residues of Sso7d selected amongst the residues located at positions which are equivalent to those listed above, is also part of the present invention. Said equivalent positions can be identified by using the file for Sso7d (chain A) in the RSCB Protein Data Bank (Berman et al., 2000) (1bf4A), and by comparing its 3D-structure with that of Sac7d (FIG. 3a):

Sac7d:7 8 9 21 22 24 26 28 29 31 33 39 40 42 44 46
1bf4A:7 8 9 21 22 24 26 28 29 31 33 40 41 43 45 47

Other proteins homologous to Sac7d can also be used for obtaining combinatorial libraries as described above. Examples of such proteins are disclosed in the following Table.

TABLE 1

Examples of Sac7d homologues which can be used according to the present invention

| Name | Source | Primary Accession number | Secondary Accession Number |
|---|---|---|---|
| Sac7d: (DNA-binding protein 7d) | Sulfolobus acidocaldarius NCBI: AAA80315 | P13123 | Q4JCI7 |
| Sac7e: (DNA-binding protein 7e) | Sulfolobus acidocaldarius NCBI: YP_255071 | P13125: | Q4JBQ1 |
| DNA-binding_protein_ 7 (DBP 7) | Sulfolobus tokodaii NCBI: Q96X56 | Q96X56 | |

TABLE 1-continued

Examples of Sac7d homologues which can be used according to the present invention

| Name | Source | Primary Accession number | Secondary Accession Number |
|---|---|---|---|
| Ssh7b (DNA-binding protein 7b) | Sulfolobus shibatae NCBI: BAA28275 | O59632 | |
| Sso7d (DNA-binding protein 7d) | Sulfolobus solfataricus NCBI: P39476 | P39476 | P81550 |
| Ssh7a (DNA-binding protein 7a) | Sulfolobus shibatae NCBI: BAA28274 | P61990 | O59631, P80170 Q9UWI8 |
| p7ss (DNA-binding protein 7a) | Sulfolobus solfataricus NCBI: P61991 | P61991 | O59631, P80170, Q9UWI8 |

Alignment of the OB-fold domains of the Sac7d homologues listed in Table 1 is shown in FIG. 4.

Other particular combinatorial libraries according to the present invention can be obtained with the Shiga-like toxin IIe (PDB 1r4pB), for example by randomizing 11, 12, 13, 14, 15 or 16 residues selected amongst the residues located at positions which are equivalent to those listed above for Sac7d, said equivalent positions (FIG. 3b) being as follows:

Sac7d:7 8 9 21 22 24 26 28 29 31 33 39 40 42 44 46
1r4pB:60 59 58 9 10 12 14 17 18 20 22 X X 27 29 31

Other examples of particular combinatorial libraries according to the present invention can be obtained by randomizing 11, 12, 13, 14, 15 or 16 residues of the human Neutrophil Activating Peptide-2 (NAP-2, PDB 1tvxA), wherein said residues are selected amongst the residues located at positions which are equivalent to those listed above for Sac7d. These equivalent positions, obtained by comparison of the 3D structure of said protein with that of Sac7d (FIG. 3c), are the following:

Sac7d:7 8 9 21 22 24 26 28 29 31 33 39 40 42 44 46
1tvxA:25 26 27 40 41 43 45 54 55 57 59 61 63 65 67 69

Still other particular combinatorial libraries according to the present invention can be obtained with the Molybdenum Binding Protein (modg) of Azotobacter vinelandii (PDB 1h9j), for example by randomizing 11, 12, 13, 14, 15 or 16 residues selected amongst the residues located at positions which are equivalent to those listed above for Sac7d, wherein said equivalent positions (FIG. 3d) are as follows:

Sac7d:7 8 9 21 22 24 26 28 29 31 33 39 40 42 44 46
1h9jA:60 61 62 86 87 89 91 93 94 96 98 105 106 108 110 112

The present invention also pertains to the use of a combinational library as those described above, for engineering a molecule specifically binding to a target. In the present text, a molecule is considered as a "specific" binder of a target, if it binds to it with a signal to noise ratio superior to 10. A binder molecule which is engineered by using a combinatorial library according to the invention preferably binds to its target (also called "target of interest") with a high affinity, i.e., with an affinity better than 10 nM when the target is a peptide or a protein, and better than 1 μM when the target is a carbohydrate molecule, for example.

Another object of the invention is a process for engineering a molecule specifically binding to a target, comprising a step of selecting, in a combinational library as described above, those variants of said OB-fold protein which specifically bind to said target. By "variant" is herein meant a protein belonging to the library, i.e., a protein which is derived from the starting OB-fold protein by mutations in its binding site.

As already mentioned above, one of the interests of the present invention is that it enables the engineering of a molecule which specifically binds to a target of interest, with virtually no limitation concerning this target. For example, the target of interest can be a peptide, a protein, an oligosaccharide, a lipid, a lipopeptide, a carbohydrate (for example, a sugar), a single-stranded DNA, a double-stranded DNA, a RNA. Interestingly, the target of interest can be a natural or synthetic small molecule, limited to a few atoms, or even to only one atom. Examples of such small molecules include any kind of haptens (i.e., small molecules which can elicit an immune response only when attached to a large carrier), vitamins, or metallic ions. The wide diversity of molecules that can be used as targets is especially interesting, since the OB-fold proteins binding to these targets can be used either for the same applications as already known for antibodies, or for different applications. For example, OB-fold proteins obtained according to the present invention and binding to metallic ions can be used in bioremediation processes, for example to remove heavy metals from a complex material such as soil or polluted water.

The skilled artisan can use any technique of the art to perform the selection step of the process according to the invention and/or to perform the screening step for obtaining a protein with a desired property. Selection techniques can be, for example, phage display (Smith, 1985), mRNA display (Wilson et al., 2001), bacterial display (Georgiou et al., 1997), yeast display (Boder and Wittrup, 1997) or ribosome display (Hanes and Pluckthun, 1997).

Ribosome display is particularly advantageous for performing the selection step, since it is performed completely in vitro and thus circumvents many limitations of in vivo systems (especially regarding the library size) (He and Taussig, 2002; Schaffitzel et al., 1999). The skilled artisan will find in the experimental part below, as well as in the articles by He and Taussig (2002), and Schaffitzel et al. (1999), or in other articles and manuals, protocols for performing ribosome display.

In a preferred embodiment of the process of the invention, 2, 3, 4 or 5 rounds of selection are performed by ribosome display.

As described in the experimental part, the process according to the invention can also comprise a further step of isolating and characterizing one or several molecules specifically binding to the target of interest. For example, the isolation and characterization steps can be performed as follows:
(i) mRNAs from a pool selected by ribosome display are reversed-transcribed and amplified by PCR, and the resulting DNAs are cloned into expression vectors;
(ii) bacteria (for example, competent DH5c) are transformed by said expression vectors (comprising said DNAs) and individual clones are grown; and
(iii) proteins extracted from said bacterial clones are tested for their binding to the target and/or other biological properties (such as stability and the like).

The clones expressing the proteins which have the best properties can then be grown to produce larger amounts of proteins. The coding sequence of the engineered protein can be determined by sequencing the pertinent part of the expression vector, and the gene encoding this protein can also be used for further engineering of the protein. Indeed, it can be advantageous to use a binder obtained through a process according to the invention to construct multifunctional proteins having at least one targeting moiety and another moiety with catalytic, fluorescent, enzymatic or any other kind of activity. This can be made, for example, through the construction of a fusion protein comprising, as a first moiety, the isolated and characterized molecule, and at least a second moiety. This second moiety can be advantageously selected amongst enzymes, markers or reporter proteins (such as PhoA, GFP and the like), therapeutic proteins, etc. According to a variant of the process of the invention, several binders are linked together (either in a fusion protein, or through non-covalent links), in order to construct fusions or complexes with multiple binding specificities.

Other objects of the invention are proteins obtained through a process as described above. In particular, proteins which specifically bind to PulD, and which have a sequence selected amongst SEQ ID Nos: 2 to 8, are part of the present invention, as well as the GarA-binder of SEQ ID No: 47.

The invention is further illustrated by the following figures and examples.

BRIEF DESCRIPTION OF THE DRAWINGS

FIG. 3a, FIG. 3b, FIG. 3c and FIG. 3d: Schematic representation and superimposition with Sac7d of a) Sso7d (structure file: 1bf4); b) Shiga-like toxin He (structure file: 2bosa); c) human Neutrophil Activating Peptide-2 (NAP-2, structure file: 1tvxA); d) Molybdenum Binding Protein (modg) of *Azotobacter vinelandii* (structure file: 1h9j). Now bene: for proteins which comprise additional domains different from the OB-fold domain, only the OB-fold domain is shown in the figure. The structure superimpositions were obtained using DALI and DALI Lite servers. The protein sequences, with their numbering in the NCBI file, are shown in Table 2 below.

TABLE 2

Figure 3A:
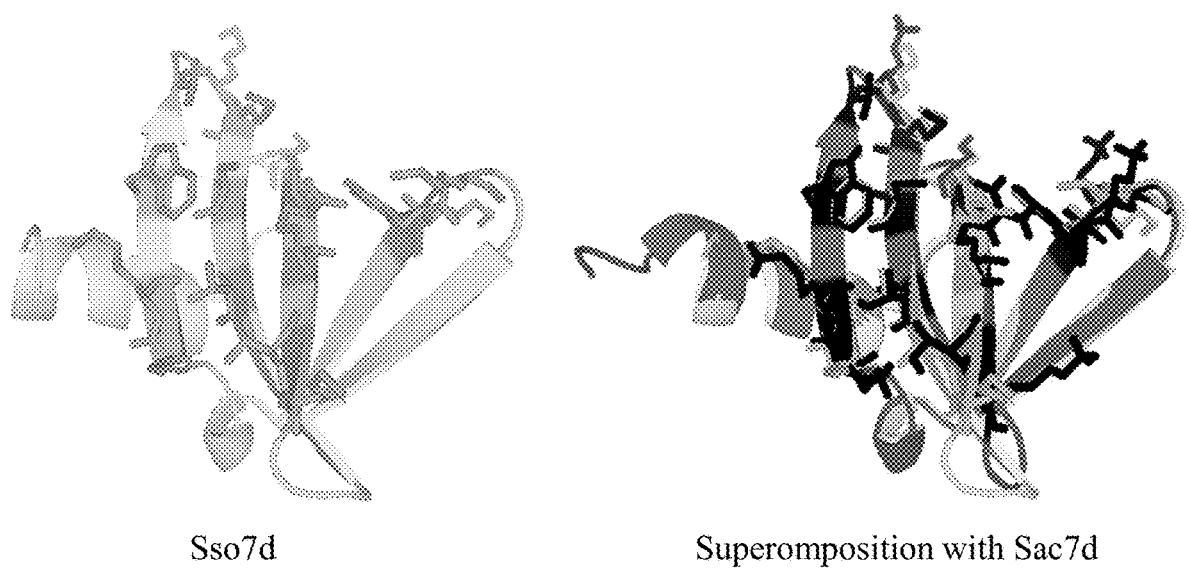

Protein sequences which have been used for obtaining the superimpositions shown in FIG. 3. The sequence fragments in italics correspond to the sequences effectively used in the structure file used to determine the positions which could advantageously be randomly mutated. Said mutation positions are in bold.

| Name | File ref. | Source | Sequence |
|---|---|---|---|
| Sac7d | 1azp | NCBI: AAA80315 | MVKVKFKYKGEEKEVDTSKIKKVWRVGKMVS FTYDDNGKTGRGAVSEEDAPKELLDMLARAE REKK (SEQ ID No: 1) |
| Sso7d | 1bf4 | NCBI: P39476 | MATVKFKYKGEEKEVDISKIKKVWRVGKMIS FTYDEGGGKTGRGAVSEKDAPKELLOMLEKO KK (SEQ ID No: 28) |
| Toxin Ile | 1r4pb | NCBI: CAA90631 | MKKMFMAVLFALVSVNAMAADCAKGKIEFSK YNEDDTFTVKVDGKEYWTSRWNLQPLLQSAQ LTGMTVTIKSSTCESGSGFAEVQFNND (SEQ ID No: 29) |
| NAP-2 | 1tvxA | NCBI: CAG33086 | MSLRLDTTPSCNSARPLHALQVLLLLSLLLT ALASSTKGQTKRNLAKGKEESLDSDLYAELR CMCIKTTSGIHPKNIQSLEVIGKGTHCNQVE VIATLKDGRKICLDPDAPRIKKIVQKKLAGD ESAD (SEQ ID No: 30) |
| modg | 1h9j | NCBI: CAA90038 | MKISARNVFKGTVSALKEGAVNAEVDILLGG GDKLAAVVTLESARSLQLAAGKEVVAVVKAP WVLLMTDSSGYRLSARNILTGTVKTIETGAV NAEVTLALQGGTEI TSMVTKEAVAELGLKPG ASASAVIKASNVILGVPA (SEQ ID No: 31) |

FIG. 4: Alignment of the OB-fold domains of several Sac7d homologues. FIG. 4 discloses SEQ ID NOS: 33-38, respectively, in order of appearance.

FIG. 5: Gene synthesis of the mutated sequences encoding Sac7d. Positions randomized for the library 11 are labelled in black. Additional randomized positions for library 14 are labelled in grey. Oligonucleotides used are represented with thin arrows (see text for their sequences). The large arrow corresponds to the coding sequence of Sac7d (without the C-ter TolA linker).

Figure 6B:
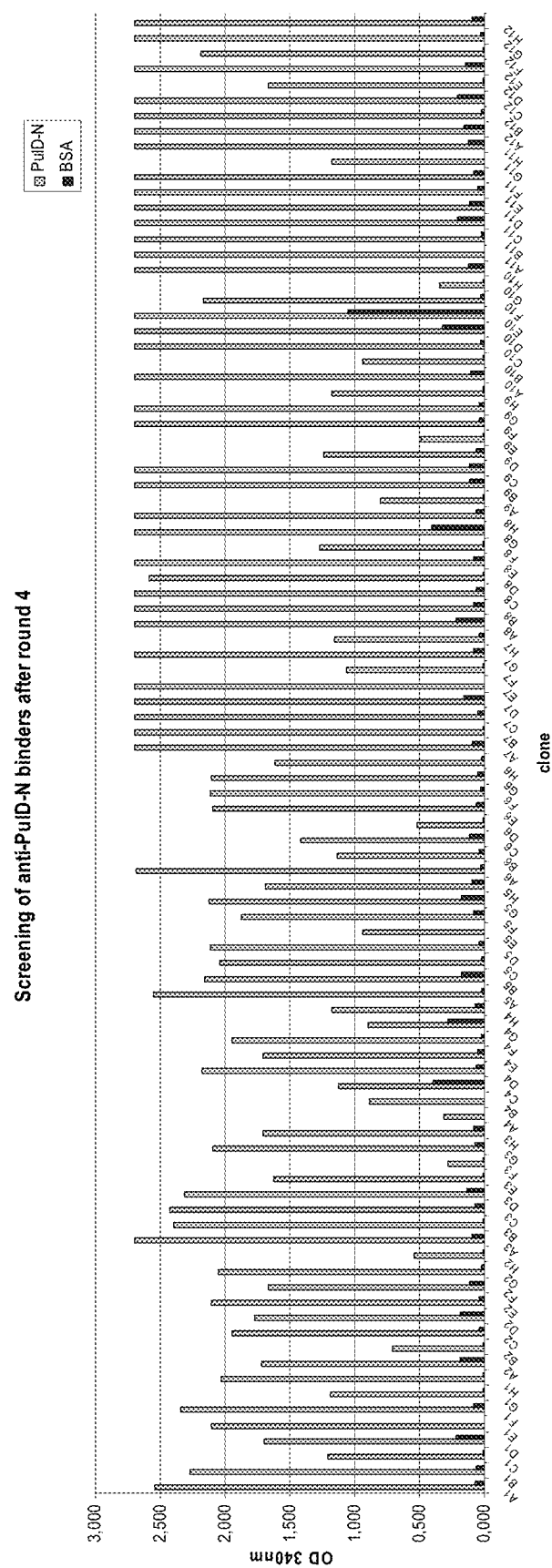
Figure 6C:
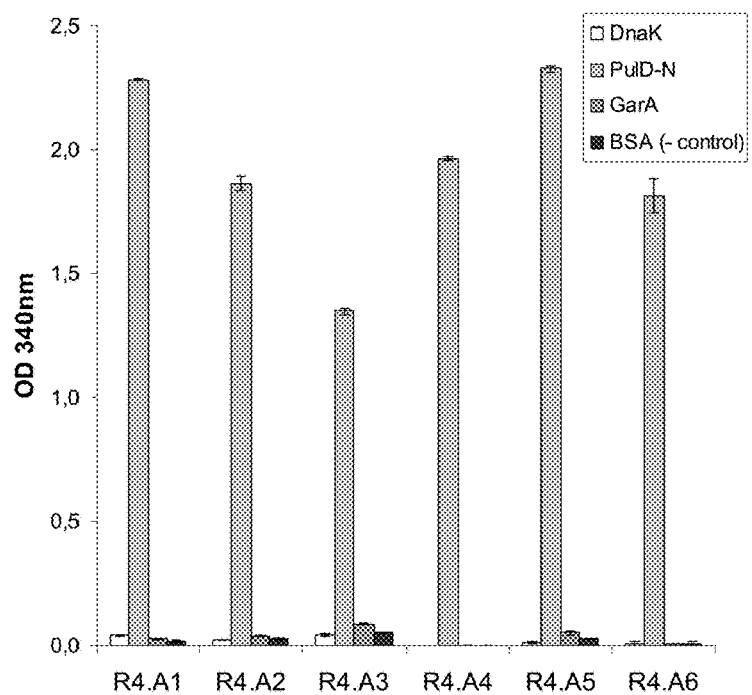

FIG. 6a, FIG. 6b, and FIG. 6c: a) RIA (radioimmuno assay) after four rounds of selection with library 11 against DnaK, PulD-N and GarA. Pools of selections were translated in vitro in presence of methionine $^{35}$S and were tested for binding to DnaK, PulD-N or GarA immobilized in an ELISA plate. After washing and elution with 0.1 M triethanolamine, amounts of binders were estimated with a β counter. Competitions were carried out in parallel with pre-incubation of translated pools with free proteins at concentrations of 1 µM and 10 µM. b) Screening of anti-PlulD-N binders after round 4. c) Test of binding specificities for six anti PulD-N binders by ELISA. Interaction between binders and immobilized DnaK, PulD-N, GarA and BSA were compared.

Figure 7:
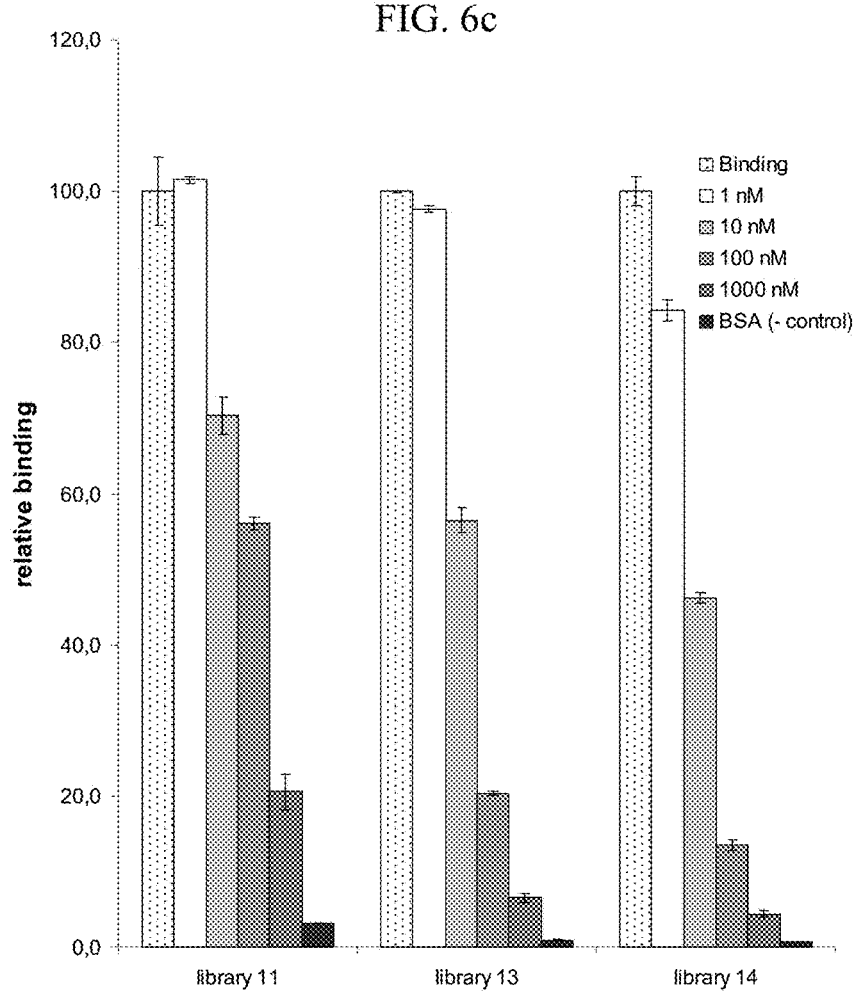

FIG. 7: RIA after five rounds of selection with libraries 11, 13 and 14 against PulD-N. Pools of selections were translated in vitro in presence of methionine $^{35}$S and were tested for binding to DnaK, PulD-N, GarA or BSA immobilized in an ELISA plate. After washing and elution 0.1 M triethanolamine, amounts of binders were estimated with a β counter. Competitions were carried out in parallel with pre-incubation of translated pools with free PulD-N at 1 nM, 10 nM, 100 nM, 1000 nM. BSA was used as negative control for binding of pools (no competition done).

FIG. 8: Sequences of eight selected binders against PulD-N. The sequence of the wild type Sac7d is shown at the top of the figure. Residues common to the wild type Sac7d and binders are represented by a dot. Positions that were programmed in the substitution scheme are highlighted in grey. FIG. 8 discloses SEQ ID NOS: 33 and 39-46, respectively, in order of appearance.

Figures 9A, 9B, 9C:
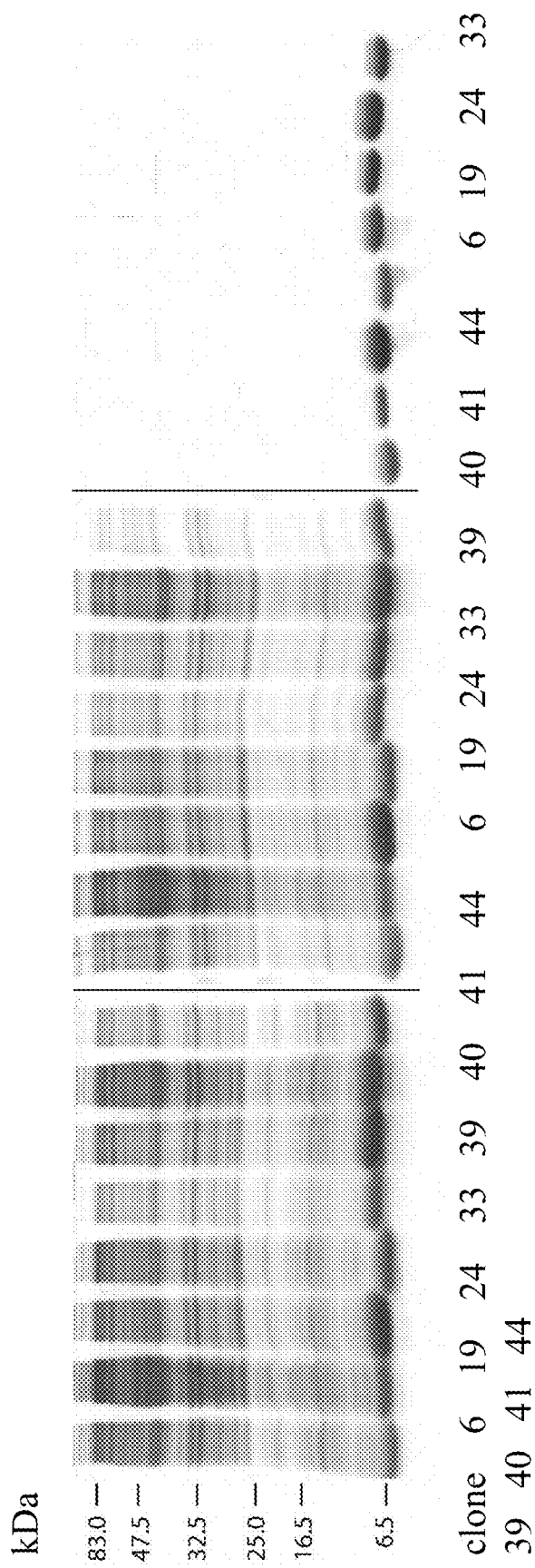

FIG. 9(a), FIG. 9(b) and FIG. 9(c): Expression and purification analysis of eight selected binders. Proteins were loaded on a 15% SDS-PAGE stained with coomasie brilliant blue. a) E. coli crude extract after expression at 30° C. Cells were harvested after 19 h induction with 0.5 mM IPTG and lyzed in loading buffer. b) Soluble fractions of crude extracts prior to purification of binders. c) Purified binders after one step IMAC (immobilized metal ion affinity chromatography) purification of the E. coli crude extract soluble fraction. All loaded samples were equivalent to 13 µl liquid culture.

Figure 10A:
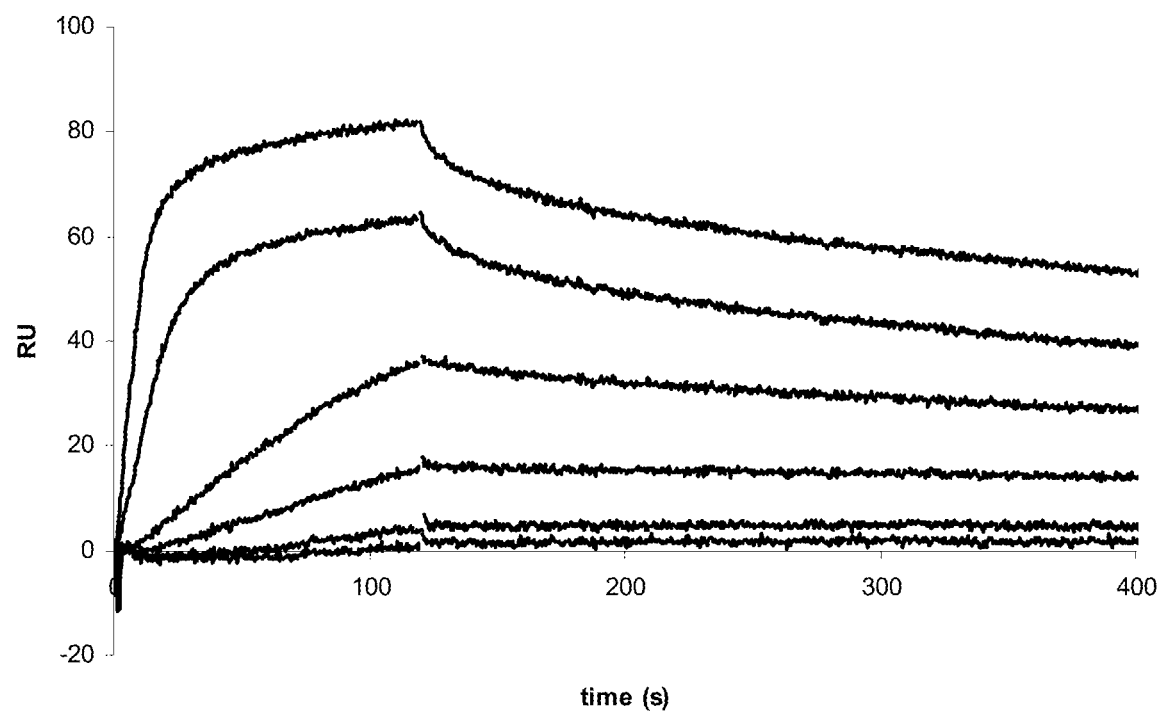
Figure 10B:
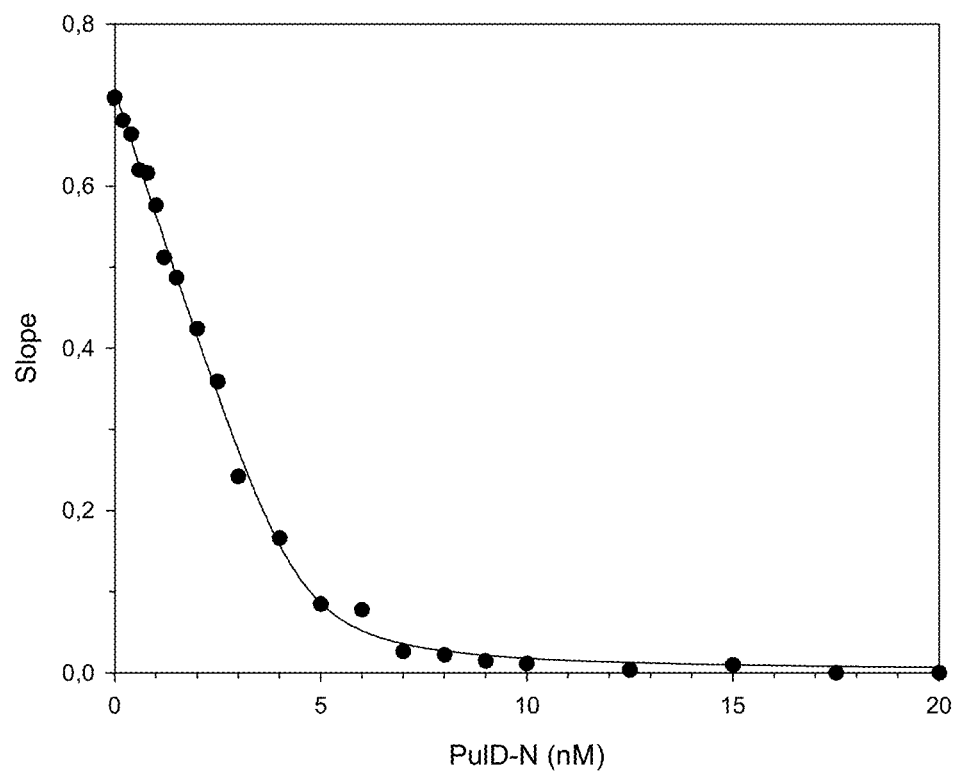

FIG. 10a and FIG. 10b: Affinity determination of clone 6 using SPR (surface plasmon resonance) analysis. a) The kinetics of binding were followed using a BIAcore. Biotinylated PulD-N was immobilized (250 RU) on a streptavidin chip and clone 6 was injected at 50 nM, 25 nM, 12.5 nM, 6.25 nM, 3.13 nM and 1.56 nM. A flow cell without immobilized PulD-N was used to control that no specific binding occurred and the signal from cell was subtracted to the one obtained from the measurement cell. BIAevaluation software was used to analyze data with a global fitting procedure. b) The affinity was also measured at equilibrium using competition BIAcore. The determined parameters from both approaches are reported in Table 3.

Figure 11:
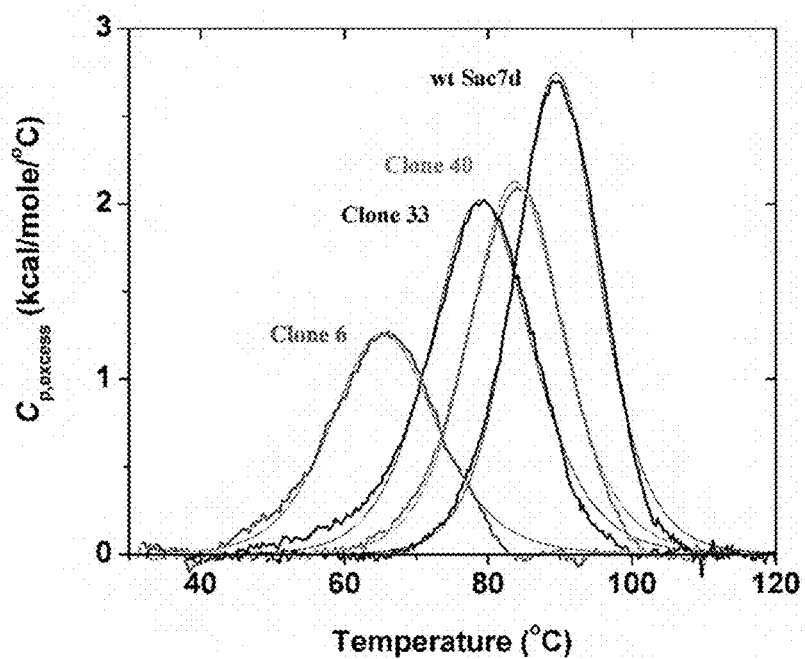

FIG. 11: Thermal stabilities of wild-type and variants Sac7d recombinant proteins determined by differential scanning calorimetry. The excess heat absorption of wt Sac7d, clone 40, clone 33, and clone 6, are reported at 1° C./min at a protein concentration of 200 µg/ml in 50 mM MES buffer pH 5.6 with 300 mM NaCl. For each protein sample, the experimental excess heat capacity curve (thick line) was best fitted to a non two-state model (thin line) by non-linear regression. Resulting thermodynamic parameters are given in Table 4.

Figure 12A:
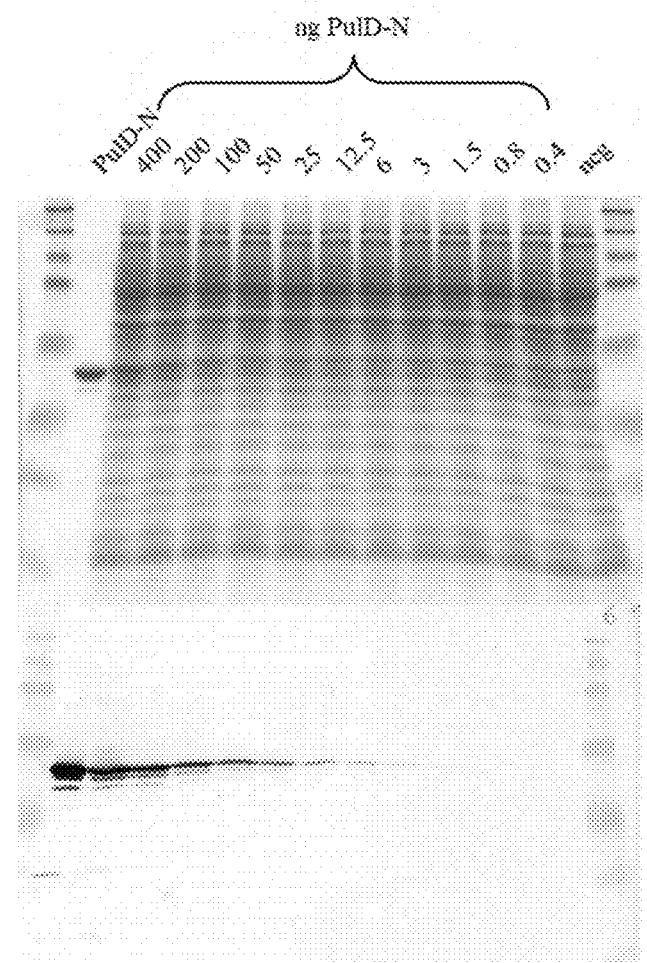
Figure 12B:
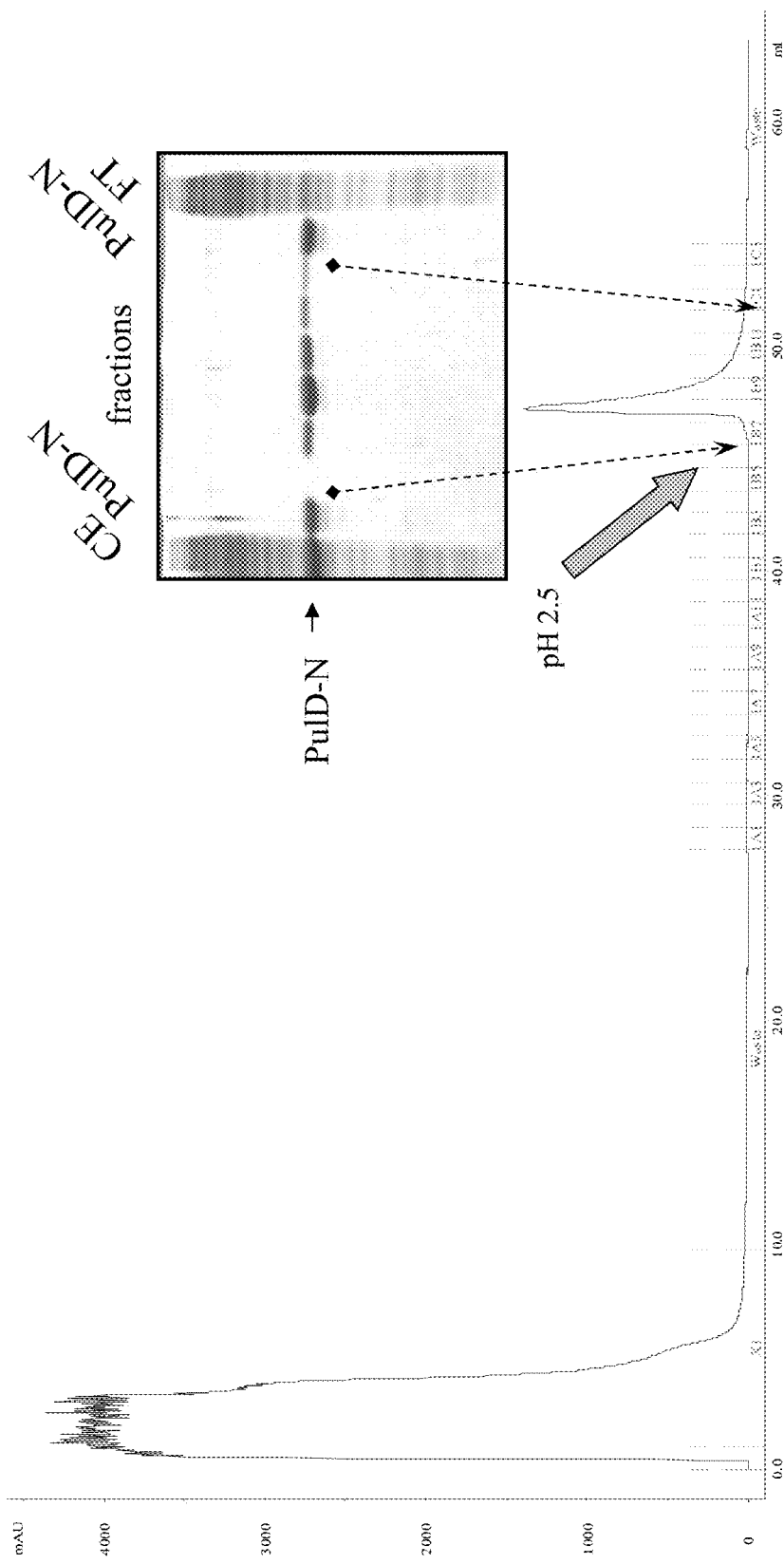

FIG. 12a and FIG. 12b: a) Western blot for detection of PulD-N mixed with *E. coli* crude extract using clone 6-alkalin phosphatase fusion. b) Single step purification of PulD-N with clone 6 immobilized on a column. The soluble fraction of an *E. coli* extract containing PulD-N was injected on the column equilibrated with HBS buffer pH7.0. After washing, the pH was dropped to 2.5 with a glycine-HCl buffer. Fractions were analyzed on a 15% SDS-PAGE and stained with coomasie brilliant blue. CE: cell extract; PulD-N: pure protein used as marker; Fractions: eluted fractions from the column after acidic pH jump; FT: flow through.

Figure 13:
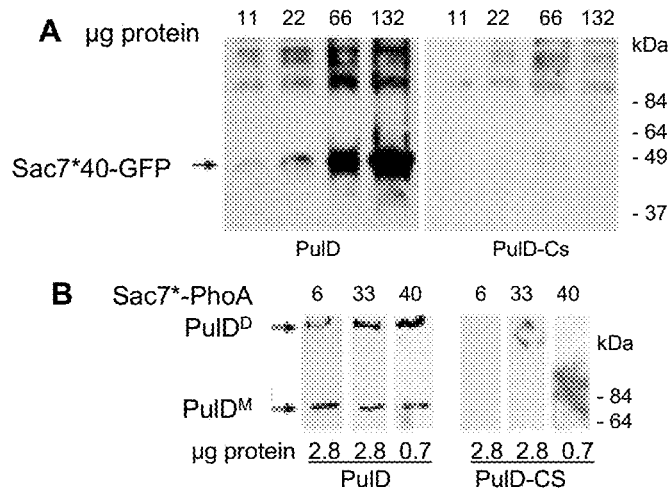

FIG. 13(A) and FIG. 13(B): Binding of Sac7*40, Sac7*33, and Sac7*6 to isolated cell envelopes and to PulD dodecamers (PulDD) and PulD monomers (PulDM). (A) Increasing amounts of cell envelope from strain PAP105 producing PulD and PulS or PulD-CS and PulS were incubated with Sac7*40-GFP, and the membrane fraction was then analyzed by SDS and immunoblotting with GFP antibodies. (B) Far-Western blotting of the indicated amounts of cell envelope proteins from the same strains using the three Sac7*-PhoA chimeras and antibodies against PhoA FIG. 14(A), FIG. 14(B) and FIG. 14(C): Production of Sac7-PhoA chimeras with and without IPTG induction and their effects on secretion and PulD multimerization in cell envelope protease-deficient strain PAP5198 carrying pCHAP231. (A) Sac7-PhoA levels detected by immunoblotting (with PhoA antibodies) of the same amount of cell extract. (B) Levels of secretion (%) and presence of PulD dodecamers (PulDD) and monomers (PulDM) detected by immunoblotting of phenol-treated and nontreated cell extracts with PulD antibodies. Arrows indicate PulDM detected without phenol treatment. S indicates Sac7d-PhoA. (C) As B, but without IPTG induction.

Figure 15:
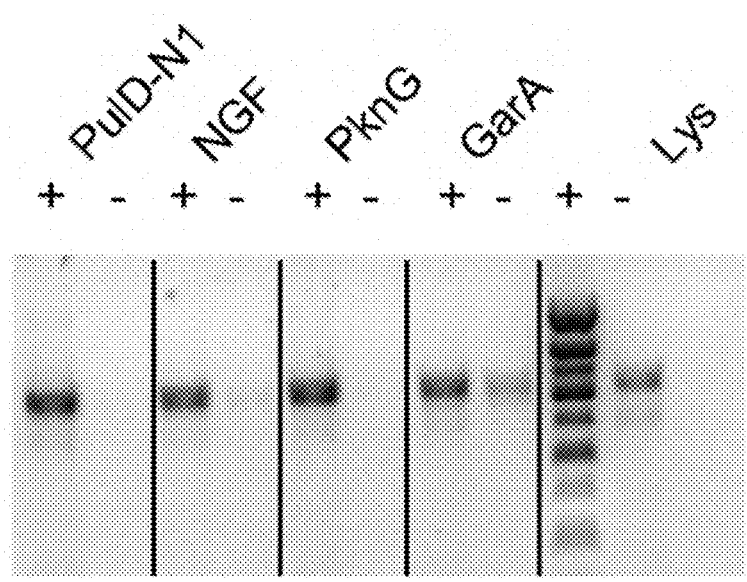

FIG. 15: PCR carried out on ADNc obtained from ARNms, eluted during cycle No. 4 (see FIG. 19, RT-PCR stage).

Figure 16:
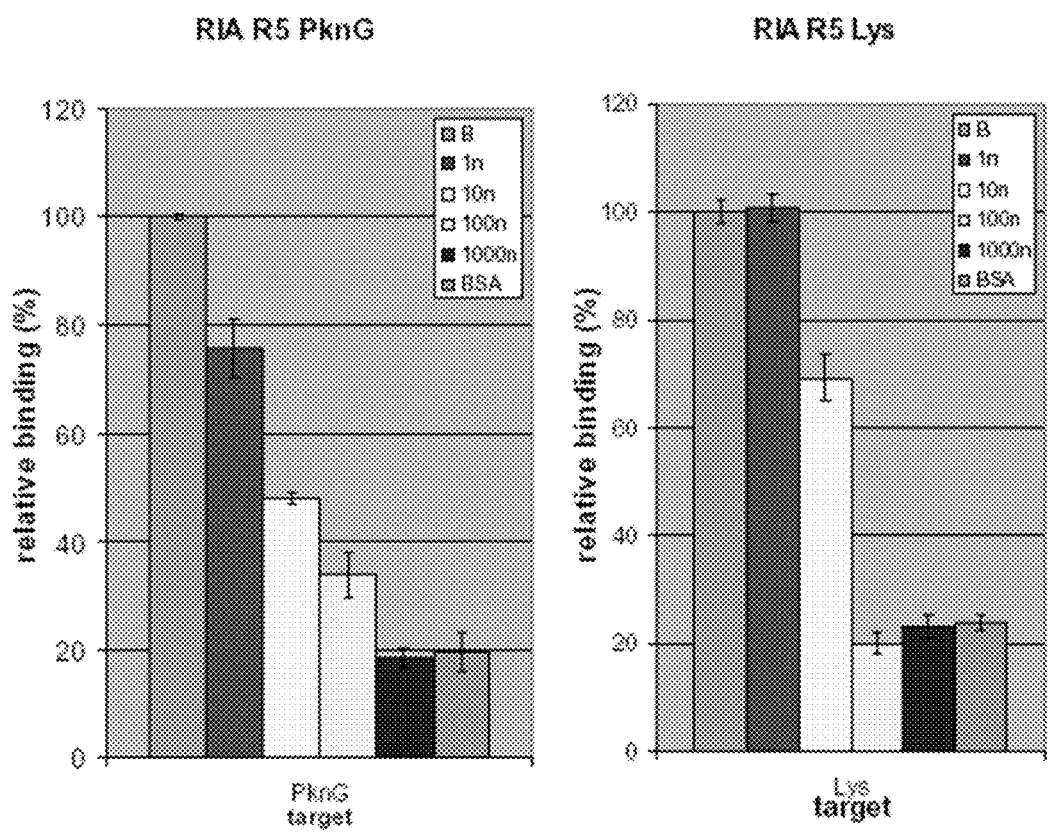

FIG. 16: competitive radio-immune tests carried out after five anti-PKnG and anti-lysozyme selection cycles.

Figure 17A:
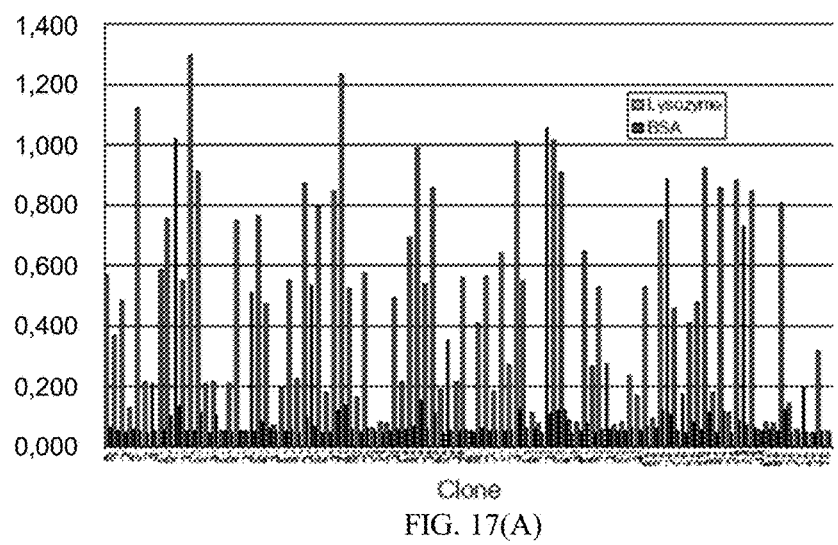
Figure 17B:
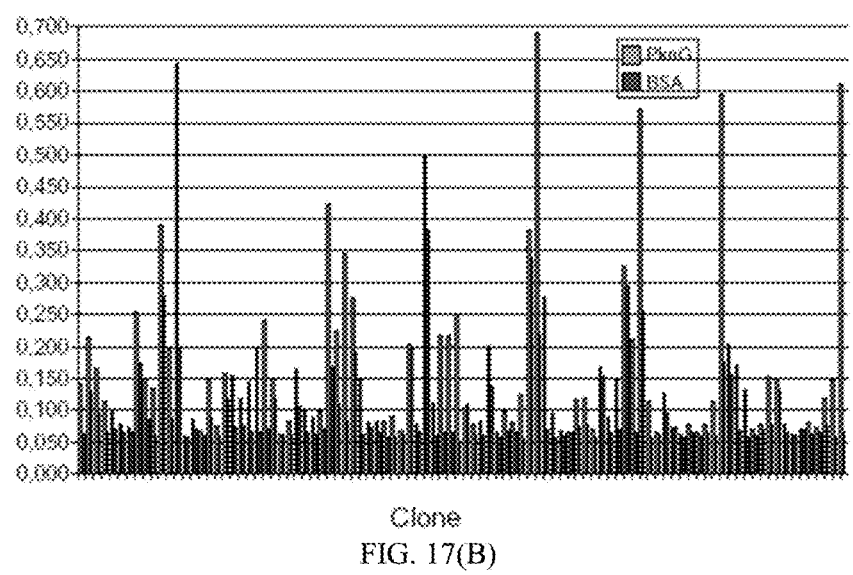
Figure 17C:
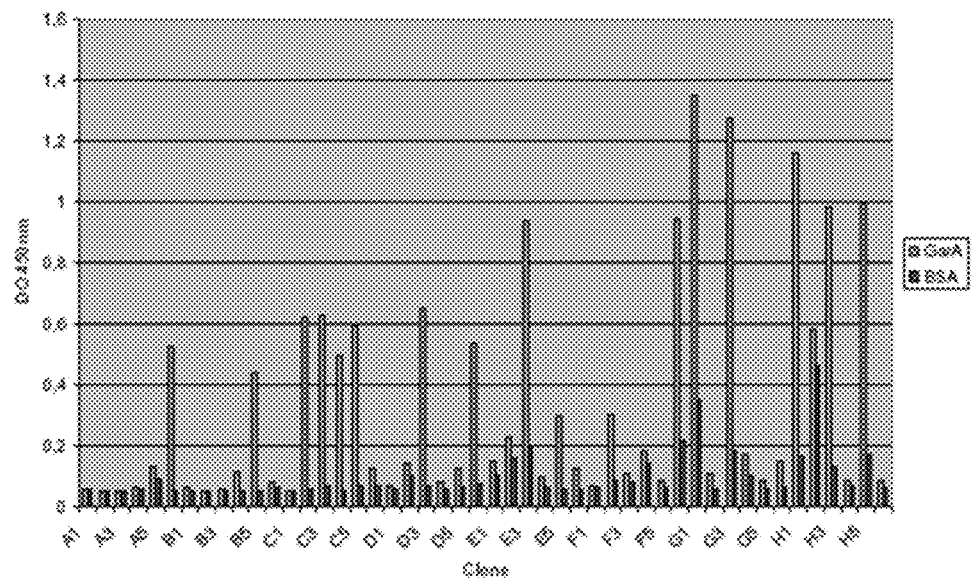
Figures 18, 19, 20:
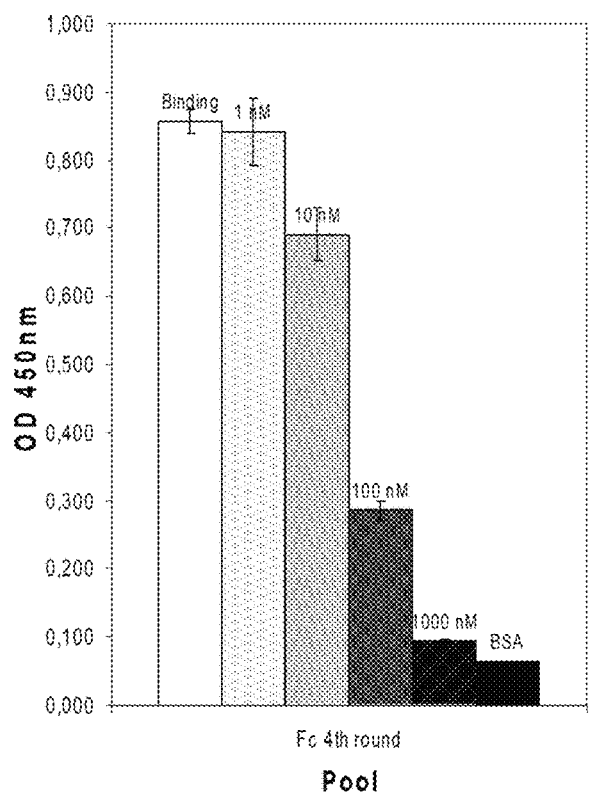

FIG. 17(A), FIG. 17(B) and FIG. 17(C): ELISA screening of anti-lysozyme (A), anti-PknG (B) and anti-GarA (C) clones obtained after 5 selection cycles FIG. 18: anti-lysozyme clone sequences obtained after five selection cycles. FIG. 18 discloses SEQ ID NOS: 49-61, respectively, in order of appearance.

FIG. 19: Alignment of a GarA-binder with Sac7d. FIG. 19 discloses SEQ ID NOS: 62, 47 and 63, respectively, in order of appearance.

FIG. 20: Competition ELISA after the 4th round of selection against Fc fragment.

Figure 21:
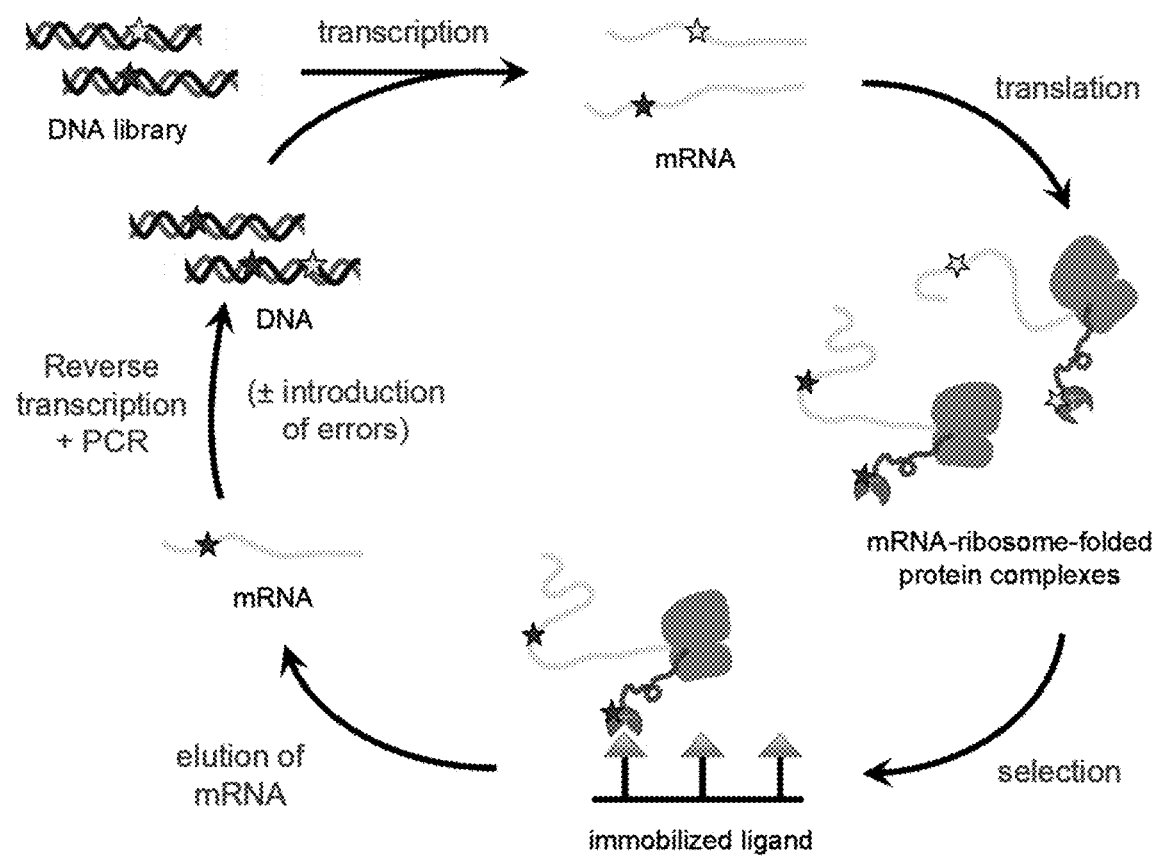

FIG. 21: Schematic representation of a round of ribosome display selection.

EXAMPLES

The experimental data which follow have been obtained using the material and methods described below.
Materials and Methods
 General Molecular Biology
 Enzymes and buffers were from New England Biolabs (USA) or Fermentas (Lithuania). Oligonucleotides were from MWG Biotech (Germany) All PCRs (polymerase chain reactions) were performed using Vent polymerase if not indicated in the text. The cloning and expression vector for the wild-type Sac7d and selected mutants was pQE30 from Qiagen (Germany).
 Synthesis of the DNA Encoding the Wild Type Sac7d
 DNA Sequence of the wild type Sac7d was generated by assembly PCR using the six following oligonucleotides: SC1 (SEQ ID No: 9: GAAACTCCTAGGTATTGTGCTGACGACCCCGATCGC-GATCTCTAGCTTTGCGGTG AAAGTGAAATT), SC2 (SEQ ID No: 10: GATCTTGCTGGTGTC-CACTTCTTTTTCTTCGCCTTTATATTTAAATTT-CACTTTCAC CGCAAAGCTAG), SC3 (SEQ ID No: 11: GAAGTGGACACCAGCAAGAT-CAAGAAAGTTTGGCGTGTGGGCAAAATGGTGAGC TTTACCTACGACGACAACGGCAAG), SC4 (SEQ ID No: 12: CTCTTTCGGGGCATCTTTCTCGCT-CACGGCGCCACGGCCGGTCTTGCCGTTGTCGT CGTA), SC5 (SEQ ID No: 13: GAGAAA-GATGCCCCGAAAGAGTTATTAGATATGT-TAGCGCGTGCGGAAAGCTTC AACCA), SC6 (SEQ ID No: 14: TGGTGGTTGAAGCTTTCCGCACG). The purified PCR product served as template for a second PCR amplification using the two following primers: SC07 (SEQ ID No: 15: ATTAATGGTACCGGATCCGTGAAAGT-GAAATTTAAATATAAAG) and SC08 (SEQ ID No: 16: ATAATTGAGCTCTAAGCTTTTTTT-CACGTTCCGCACGCGCTAACATATC). The PCR product was cloned into pQe30 expression vector using BamHI and HindIII restriction sites. A clone with the expected sequence was used for subsequent expressions.
 Generation of Combinatorial Libraries
 The protocol was the same for the generation of the three libraries 11, 13, 14 in a format compatible with ribosome display. Libraries were mainly constructed by gene synthesis and PCR assembly steps. With a single step PCR using a combination of four standards and three degenerated oligonucleotides encoding NNS triplets (wherein N=A, C, T or G, and S=C or G), a DNA product including the 5'-flanking region necessary for ribosome display and the randomized gene of Sac7d was obtained. For the library 14, the following oligonucleotides were used: T7C (SEQ ID No: 17: ATACGAAATTAATACGACTCACTATAGGGAGAC-CACAACGGTTTCCCTC), SDA_MRGS (SEQ ID No: 18: AGACCACAACGGTTTCCCTCTAGAAATAAT-TTTGTTTAACTTTAAGAAGGAGATA TATCCAT-GAGAGGATCG), SClib1 (SEQ ID No: 19: GGAGA-TATATCCATGAGAGGATCGCATCACCATCACCATCA-CGGATCCGTCAAGG TGAAATTC), SClib2 (SEQ ID No: 20: GGATCCGTCAAGGTGAAAT-TCNNSNNSNNSGGCGAAGAAAAAGAAGTGGACACT AGTAAGATC), SClib3 (SEQ ID No: 21: CTTGCCGTTGTCGTCGTASNNAAASNN-CACSNNTTTGCCSNNACGSNNAACSNNSN NGATCT-TACTAGTGTCCACTTC), SClib4 (SEQ ID No: 22: TAATAACTCTTTCGGGGCATCTTTCTCSNN-CACSNNGCCSNNGCCSNNCTTGCCGT TGTCGTCGTA), SClib5 (SEQ ID No: 23: CCATATAAAGCTTTTTCTCGCGTTCCGCACGCGCTAA-CATATCTAATAACTCTTTC GGGGCATC). Primers encoding wild-type triplets instead of NNS triplets at positions corresponding to residues 21, 22 and 40, or to residue 40 in Sac7d were used for the construction of libraries 11 and 13, respectively.
 To the aim that the protein displayed on ribosome be accessible to potential ligands, the protein needs to be fused to a linker. The sequence of this linker, corresponding to a part of the *E. coli* protein TolA, encoded in the plasmid pRDV vector (Binz et al., 2004a), was PCR-amplified using primers SClink (SEQ ID No: 24: GCGGAACGCGAGAAAAAGCTT-TATATGGCCTCGGGGGCC) and tolAk (SEQ ID No: 25: CCGCACACCAGTAAGGTGTGCGGTTTCAGTTGCCG CTTTCTTTCT) (the latter encoding the 3'-flanking region necessary for ribosome display). Finally the library was assembled with tolA linker by PCR assembly using tolAk and T7B (SEQ ID No: 25: ATACGAAATTAATACGACT-CACTATAGGGAGACCACAACGG) primers. The final assembly product corresponded to a library of Sac7d with all the 5'- and 3'-regions necessary to its use for ribosome display selections as previously described (Hanes et al., 1998; Schaffitzel et al., 1999).

Ribosome Display Selection Rounds

For selection experiments, biotinylated target proteins were used. The biotinylation was performed by incubation of a 10 µM solution of DnaK, GarA or PulD-N with a 20-fold molar excess of Sulfosuccinimidyl-6-(biotinamido) hexanoate (Sulfo-NHS-LC-LC-Biotin, Pierce) in PBS on ice for 1 h. The biotinylated proteins were buffer-exchanged using protein desalting spin columns from Pierce equilibrated in TBS. The degree of biotinylation was determined using the HABA assay (Sigma) as from 2 to 3 molecules biotin per protein molecule. Biotinylated target proteins were bound to immobilized neutravidin in a Maxisorp plate (Nunc) and selections by ribosome display were performed at 4° C. essentially as described (Binz et al., 2004b) with some modifications. Briefly, after each round of selection the eluted mRNA was reverse-transcribed to cDNA and amplified using SDA_MRGS and SClib5 primers. The PCR product was desalted on a Nuclespin ExtractII column (Macherey-Nagel) and used for a PCR assembly with TolA-linker DNA fragment (see above). This generated a full length ribosome display construct with newly added 5'- and 3'-flanking regions to minimize loss of clones due to degradation of the extremities of mRNA during its manipulation. The number of RT-PCR cycles were 35 cycles (round 1), 30 cycles (round 2), 30 cycles (round 3), 25 cycles (round 4). In round five, the selection pressure was increased using off-rate selection as described (Jermutus et al., 2001). For this selection, 10 nM of biotinylated PulD-N was added to the stopped translation of the pool from round 4. The mix was equilibrated 1 h at 4° C. and non-biotinylated PulD-N was added to a final concentration of 10 µM (1000 fold excess over biotinylated PulD-N). After 2 h incubation at 4° C. with agitation, the ternary complexes (mRNA-ribosome-binder) bound to biotinylated PulD-N were capture with 30 µl of magnetic streptavidin coated beads (Roche) 15 min at 4° C. Beads were washed and mRNA was isolated as for the first four rounds. The number of RT-PCR cycles was 35 for this 5$^{th}$ round of selection. Progresses of selections were checked by monitoring the amounts of RT-PCR products from round to round.

Analysis of Selected Pools and Isolated Clones

After four or five rounds, selected pools were tested by RIA (radioimmuno assay) as described (Hanes et al., 1998) using directly coated target protein in a Maxisorp plate and using from 1 nM to 10 µM of free target protein as competitor.

The RT-PCR products from selected pools were cloned into pQE30 vector using BamHI and HindIII restriction sites and the resulting ligations were used to transform *E. coli* DH5α strain. Clones were picked from Petri dish to inoculate a deep-well plate containing 1.5 ml of LB medium per well (100 µg/ml ampicillin, 1% glucose). After overnight culture at 37° C. with shaking at 250 rpm, 0.2 ml of each well from this master plate was used to inoculate an other deep-well plate containing 1.3 ml 2YT medium (100 µg/ml ampicillin) per well. The plate was then incubated at 37° C. for 1 h with shaking (250 rpm). The expression was induced with the addition of 0.5 mM IPTG and incubation at 30° C. for 4 h with shaking (250 rpm). Cells were pelleted with a centrifugation step (2250 g) and supernatants discarded. Proteins were extracted with 50 µl BugBuster (Novagen) per well with shaking at 250 rpm for 30 min, then 250 µl of TBS pH 7.4 (20 mM Tris-HCl, 150 mM NaCl) were added. Cell debris were pelleted with a centrifugation step (2500 g). For ELISA (enzyme-linked immunosorbent assay) screening, 100 µl of each supernatant were used to test the binding on target proteins coated into a Maxisorp plate. The detection was performed using the RGS His antibody HRP conjugate (Qiagen) that detects only the RGS-(His)$_6$-tag from binders and not the (His)$_6$-tag from target proteins and BM-Blue substrate from Roche. All incubation steps were carried-out in TBS pH 7.4 with 0.1% Tween 20. Positive clones were sequenced by standard sequencing techniques.

Protein Production for Screening by SPR (Surface Plasmon Resonance)

To perform the screening of binders based on their time of dissociation from PulD-N, clones were expressed in a 5 ml scale culture (*E. coli* DH5α strain). Five hundreds microliters of an overnight preculture (LB medium, 100 µg/ml ampicillin, 1% glucose, 37° C.) in deepwell were used to inoculate 4.5 ml culture (2YT, 100 µg/ml ampicillin, 37° C.) in deepwell. Expression was induced at OD$_{600}$=1.0 by addition of 0.5 mM IPTG and cultures were incubated for 19 h at 30° C. (250 rpm). Cells were harvested by centrifugation (2500 g) and proteins were extracted in deepwells by resuspension of cells in 0.5 ml TBS pH 7.4 containing 25 mM immidazole, BugBuster and Benzonase (Novagen). After 1 h shaking at 4° C. the deepwell was centrifuged to pellet cell debris. Supernatants were purified on microspin columns containing 100 µl Ni-Fast Flow Chelating Sepharose (General Electric) equilibrated with TBS pH 7.4 containing 20 mM imidazole. Resin was washed 4 times with the loading buffer and purified proteins were eluted with 400 µl TBS pH 7.4 and 250 mM immidazole.

Protein Production and Purification of Binders and Wild-Type Sac7d

For Biacore and microcalorimetry experiments, the binders were expressed in DH5α *E. coli* strain in a 1 liter scale and purified as described below. Fifty milliliters of an overnight preculture (LB medium, 100 µg/ml ampicillin, 1% glucose, 37° C.) were used to inoculate 1 liter culture (2YT, 100 µg/ml ampicillin, 37° C.). Expression was induced at OD$_{600}$=1.0 by addition of 0.5 mM IPTG and cultures were incubated for 19 h at 30° C. (250 rpm). Cells were harvested by centrifugation and resuspended in 30 ml TBS pH 7.4 at 30° C. containing 25 mM immidazole. Cells were lyzed with an Avestin Emulsiflex homogenizer and cell debris were discarded with a centrifugation step. Proteins were purified on a 5 ml HiTrap chelating column equilibrated with TBS pH 7.4 containing 25 mM immidazole. Elution was performed with TBS pH 7.4 and 250 mM immidazole. Proteins were further purified by size-exclusion chromatography on a Superdex 75 26/60 gel filtration column (GE Healthcare) equilibrated with HBS pH 7.0 (20 mM HEPES, 150 mM NaCl). Analytical gel filtration were done on a SMART system (GE Healthcare) using a Superdex 75 3.2/20 column equilibrated with HBS pH 7.0 (60 µl/min, 50 µl sample injected). BPTI (6.5 kDa), Ribonuclease A (14.6 kDa), Chymotrypsinogen A (20.3 kDa), Ovalbumin (46.7 kDa)

and Albumin (62.9 kDa) were used as molecular weight gel filtration calibration standards.

Surface Plasmon Resonance

SPR was measured using a BIAcore 2000 instrument at 25° C. Biotinylated PulD was prepared as for selections by ribosome display and immobilized on flow cells of a SA-chip. The densities of immobilized biotinylated PulD-N for kinetic measurements, and for inhibition measurements were 200 RU and 800 RU (saturated chip), respectively. The running buffer was HBST pH 7.0 (20 mM HEPES, 150 mM NaCl, 0.05% Tween 20).

The screening and the ranking of binders according to their off-rate were performed using micro IMAC purified proteins (see above) diluted ½0 in running buffer prior injections for kinetics measurements at a flow rate of 60 µl/min.

Kinetic measurements for affinity determinations were performed with size-exclusion purified proteins injected at concentration ranging from 1 nM to 50 nM. Inhibition measurements were done as described (Ostermeier et al., 1995) at a concentration of binder of 5 nM and different concentrations of PulD-N as a competitor in concentration ranging from 0.2 nM to 20 nM at a flow rate of 25 µl/min. The slope of the sensorgram for the binding phase was determined and plotted versus the concentration of PulD-N. Data evaluation was done using BIAeval software (BIAcore).

Microcalorimetry

Differential scanning calorimetry was performed with a MicroCal VP-DSC calorimeter as described previously (Hible et al., 2005). Stock solutions of recombinant wild-type and variants Sac7d were dialyzed overnight at 4° C. against 50 mM MES buffer (pH 5.6 300 mM NaCl). Protein samples were then diluted to 200 µg/ml in the same buffer preparation, degassed under vacuum for 10 mM with gentle stirring prior to loading into the calorimeter cell (0.5 ml). The reference cell was filled with the same buffer. Samples were held in situ under a constant external pressure of 25 psi to avoid bubble formation and evaporation up to 130° C., equilibrated for 25 mM at 25° C., heated at a constant heating rate of 1 deg./min, and the data collected with a 16 sec filter. Data analysis was made with the Origin7™ software (Plotnikov et al., 1997) provided by the manufacturer. The excess heat capacity function ($C_p$,excess) was obtained after subtraction of two base lines from the heat capacity function, the buffer reference thermogram and the calculated chemical base line calculated after normalizing to concentration from the progress of the unfolding transition. Thermodynamic parameters of the unfolding transitions of each protein sample are the results of non-linear three-parameter ($T_m$, $\Delta H_{cal}$, $\Delta H_{vH}$)) regression of the excess heat capacity curve assuming a non two-state model.

Construction of Alkaline Phosphatase Fusions

The genes encoding binders were PCR amplified with the primers SCPhoAF (SEQ ID No: 26: ATTAATGGTACCG-GATCCGTGAAGGTGAAATTC) and SCPhoAR (SEQ ID No: 27: ATAATTGAGCTCTAAGCTTTTTTT-CACGCTCCGCAC) and Phusion polymerase to introduce KpnI and SacI at 5'- and 3'-extremities, respectively. The PCR products were digested with KpnI and SacI and cloned into pQUANTagen vector (Qbiogene). Thus, alkaline phosphatase was fused to the C-terminus of the binder. Screening of alkaline phosphatase active clones and periplasmic extractions were performed using DH5α E. coli strain and instructions from the manufacturer manual. Briefly, positive clones were screened on LB plates (100 µg/ml ampicillin, 4 µg/ml 5-bromo-4-chloro-3-indolyl-phosphate) for their alkaline phosphate activity. Eight milliliters of an overnight preculture (LB medium, 100 µg/ml ampicillin, 37° C.) was used to inoculate a culture of 400 ml (2YT medium, 100 µg/ml ampicillin, 1 g dipotassium phosphate pH 7.5, 37° C.). Induction of the tac promoter was done with addition of 0.5 mM IPTG when $OD_{600}$ was about 0.7 and the growth was continued for 4 h at 30° C. Cells were pelleted by centrifugation and resuspended in 40 ml of TSE buffer (30 mM Tris-HCl pH 8.0, sucrose 20%, 0.5 mM EDTA, 0.1 mg/ml lysozyme). The lysozymic shock was performed by incubation of the suspension for 20 mM at 4° C. with gentle agitation. Cell debris were discarded by centrifugation for 30 mM at 20000 g at 4° C. and supernatants were filtered through a 0.45 µm membrane prior storage at –20° C.

Western Blots Using Alkaline Phosphatase Fusions

A 10 ml overnight culture of DH5α E. coli strain (LB medium, 37° C.) without any expression vector was centrifuged to pellet cells. The cell pellet was resuspended in 1 ml TBS (1× BugBuster and 1 µl Benzonase). Cell lysis occurred at room temperature for 30 mM and the suspension was centrifuged at 20000 g for 5 mM to remove cell debris. The supernatant was then used for serial dilution of purified PulD-N. Samples were prepared with a constant volume of supernatant and a variable quantity of purified PulD-N corresponding from 0.4 ng to 400 ng PulD-N when 5 µl samples were loaded on a SDS gel. After migration, proteins were transferred from SDS gel to a nitrocellulose membrane (Hybond-C extra, 0.45 µm, General Electric). The membrane was blocked with 5% dried milk in TBST (20 mM Tris-HCl, 150 mM NaCl, pH7.5, 0.1% Tween 20). The membrane was then incubated with soluble perimasplic extract of fusions diluted 1 to 15 in TBST milk for 1 h with gentle agitation. After washing the membrane, detection was done with precipitating substrate NBT/BCIP (AP conjugate substrate kit, Biorad) diluted in reaction buffer (100 mM Tris-HCl pH9.5, 100 mM NaCl, 5 mM $MgCl_2$).

Construction and Expression of GFP (Green Fluorescent Protein) Fusions

The genes encoding binders were cloned via BamHI and HindIII sites into a pQE30 derived plasmid (pFP3000) containing the gene for eGFP and a region encoding for a flexible peptidic linker KLGSAGSAAGSGEF (SEQ ID No: 32). This resulted in N-ter-binder-linker-eGFP-C-ter fusions with a MRGS $(His)_6$ tag at the N-terminus. The sequences of individual clones were checked by DNA sequencing.

Expression and purification of binder-GFP fusions were done under the same conditions as for binders alone (i.e., with an IMAC and a size exclusion chromatography step).

Isolation of Membrane Fractions and Interaction Studies with the 40-eGFP Chimera E. coli K-12 strains PAP105 (Guilvout et al., 1999) carrying the plasmids pCHAP3671(pulD) and pCHAP580 (pulS) (Guilvout et al., 1999) or plasmids pCHAP3711 (pulD-CS) (Guilvout et al., 2006) and pCHAP580 were used for the isolation of the membrane vesicles. Cultures were grown to exponentially phase ($OD_{600}$: 0.9-1.1) in LB medium (Miller, 1992) containing appropriate antibiotics (100 µg/ml ampicillin, 25 µg/ml chloramphenicol) at 30° C. with vigorous aeration. The membrane fractions were isolated by centrifugation (180,000×g for 30 mM) after French press desintegration of the cells and redissolved in Tris 50 mM pH 7.5, NaCl 150 mM at a final concentration of 450 µg/ml.

Different quantities of the membrane vesicles were incubated for 1 hour at room temperature with 70 pmol of the purified 40-eGFP fusion protein. After centrifugation (80,000×g for 20 mM) the pellets were washed with the same buffer, centrifuged again and resuspended in the same volume. The proteins in each sample were separated by SDS-PAGE and transferred onto nitrocellulose. The detection of the 40-eGFP fusion protein was performed by immunoblotting with GFP primary antibodies.

Affinity Chromatography Using Immobilized Clone 6 Binder

Seventeen milligrams of IMAC purified clone 6 was dialyzed against a 0.2 M carbonate buffer pH 8.3 (0.5 M NaCl) and was injected on a 1 ml HiTrap NHS-activated HP column (General Electric) previously flushed with 6 ml of 1 mM HCl Immobilization occurred at room temperature for 30 minutes. After washing the column and deactivating any remaining active groups with 0.5 M ethanolamine (0.5 M NaCl, pH 8.3) and 0.1 M acetate (0.5 M NaCl, pH 8.3) for 30 mM at room temperature, the column was equilibrated with TBS pH 8.0 (20 mM Tris, 500 mM NaCl) and was ready to use for purification.

PulD-N protein was expressed using BL21(DE3) E. coli strain transformed with the plasmid pCHAP3702 (Chami et al., 2005). Fifty milliliters of an overnight preculture (LB medium, 100 µg/ml ampicillin, 1% glucose, 37° C.) were used to inoculate 1 l culture (2YT, 100 µg/ml ampicillin, 37° C.). Expression was induced at $OD_{600}=1.0$ by addition of 1.0 mM IPTG and cultures were incubated for 4 h at 30° C. (250 rpm). Cells were harvested by centrifugation and resuspended in 30 ml TBS pH 8.0. Cells were lyzed with an Avestin Emulsiflex homogenizer and cell debris were discarded with a centrifugation step. One milliliter and a half of this soluble fraction was injected on the NHS-clone 6 immobilized column at a flow rate of 0.5 ml/min Non specific proteins were washed away with 40 ml of running buffer and PulD-N was eluted with an acidic pH jump using a 100 mM glycine buffer (pH 2.5, 250 mM NaCl). Purity of the eluted protein was checked by loading fractions on a SDS gel.

Far Western Blotting

Outer membranes of E. coli PAP105+/− PulD (pCHAP3671; (Guilvout et al., 1999)) or PulD-CS (pCHAP3711; (Guilvout et al., 2006)) together with PulS (pCHAP580; (Daefler et al., 1997)) were prepared as before. Membranes were resuspended and stored in 50 mM Tris-HCl, pH 7.5, containing 10% sucrose and 0.1 mg/ml of the protease inhibitor Pefabloc (Interchim, Montluçon, France) and were subjected to SDS/PAGE and transferred onto nitrocellulose sheets that were then blocked and incubated with periplasmic (osmotic shock) extracts of strains producing Sac7-PhoA chimeras. After washing, bound PhoA was detected by antibodies against PhoA, horseradish peroxidase-coupled secondary antibodies, and chemiluminescence.

Secretion

Strain PAP7232 (Hardie et al., 1996) was transformed with the empty vector or with plasmids encoding Sac7-PhoA chimeras. Transformants were grown in medium containing 0.4% maltose (to induce production of pullulanase and its secretion system, including PulD) and 1 mM IPTG to induce Sac7-PhoA production. Secretion levels were measured as described in (d'Enfert et al., 1989) and are expressed as the amount of enzyme activity detected in whole cells compared with that detected in lysed cells (100%). Cell extracts were also examined by immunoblotting with antibodies against PulD and PhoA.

To analyze the effects of the Sac7-PhoA chimeras at higher (plasmid-encoded) levels of PulD production, a zeocin resistance gene was amplified with flanking PstI sites and inserted into the unique PstI site in the blaM gene of the corresponding plasmids. The recombinant plasmids were then transformed together with pCHAP231 (d'Enfert et al., 1987) into the envelope protease-deficient strain PAP5198 (degP, ompT, ptr). Pullulanase secretion and levels of PulD (with or without prior treatment with phenol) were analyzed as above with or without induction by IPTG.

Results

Example 1: Design of the First Generation Library (Library 11)

The first critical step for investigating the possibility to use Sac7d as a scaffold for obtaining binders to various ligands was to design a library by randomization of the potential binding area, while maintaining the stability and the solubility of the parent Sac7d protein.

Figure 1A:
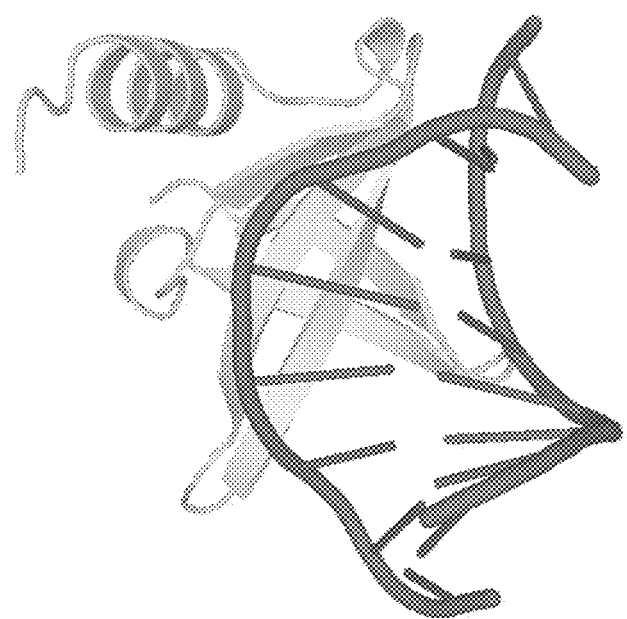
FIG. 1a and FIG. 1b: a) Schematic representation of wild type Sac7d in complex with double strain DNA (PDB code 1azp). b) Residues participating to DNA binding. The concave area is defined with residues coloured in light grey, the flat area with those coloured in medium and dark grey. The residues at limit between the regions of the binding area are coloured in medium grey.
Figure 1B:
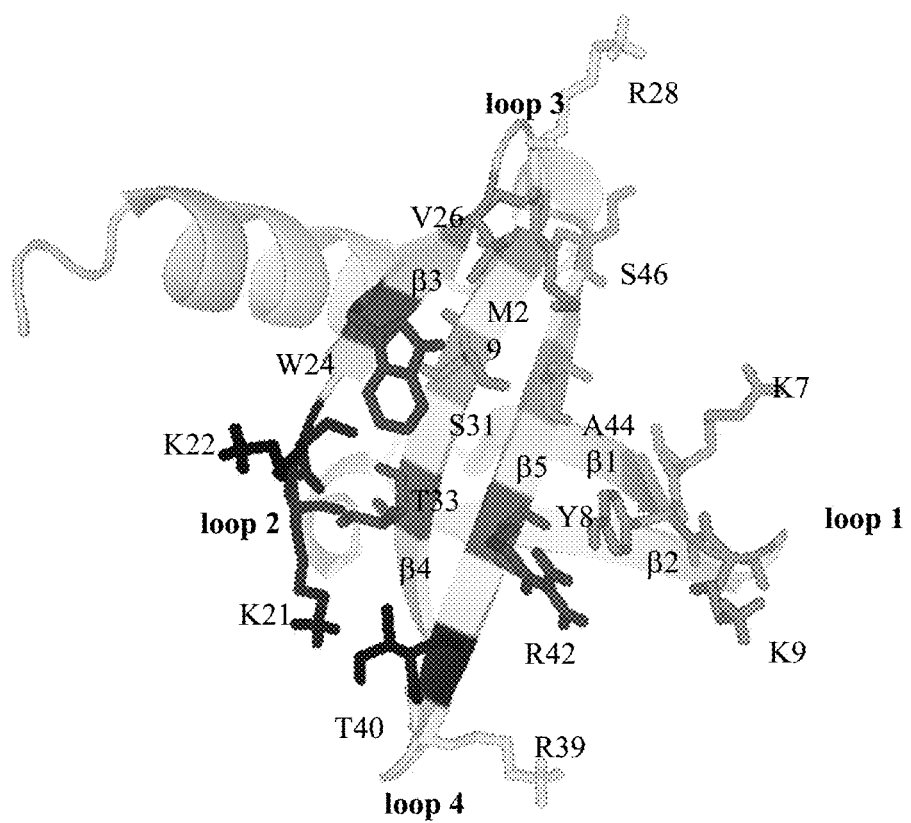

Several three dimensional structures of Sac7d-DNA complexes are known (Agback et al., 1998; Edmondson and Shriver, 2001; Gao et al., 1998; McAfee et al., 1995; McCrary et al., 1996; Robinson et al., 1998; Su et al., 2000) (FIG. 1a). According to these structures, the binding of Sac7d to minor groove of DNA involves a binding surface area that matches remarkably (shapes and charges) with DNA. This binding area is composed of sixteen residues (K7, Y8, K9, K21, K22, W24, V26, K28, M29, S31, T33, K39, T40, R42, A44, S46) (FIG. 1b). A visual inspection of this binding area shows that it is twisted and that it comprises two kinds of geometries: one lightly concave (K7, Y8, K9, W24, V26, K28, M29, S31, T33, R42, A44, S46) and the other essentially flat (K21, K22, W24, T33, K39, T40, R42). Residues W24, T33, and R42 are shared by these two surfaces. About a quarter of the sequence of Sac7d is dedicated to the binding of DNA. Although all of these residues are exposed on the surface, a massive random mutagenesis of 25% of the sequence of Sac7d could be dramatic for the folding and the stability of the mutants obtained. In a first step, the inventors decided to exclude K28 and K39 from the mutagenesis scheme, since these two residues are not fully orientated towards the binding surface. The second reason to exclude them was that generation of libraries by a one-step PCR as described below would have been impossible due to reduced overlaps available for primers annealing (see below). It was also postulated that the geometry of the concave side of the binding area could match well with the spherical shape of globular proteins, or, at least, that it could accommodate binding of their exposed loops. Thus, the substitution strategy focused on the eleven residues in this region of Sac7d (K7, Y8, K9, W24, V26, M29, S31, T33, R42, A44, S46).

The gene coding for Sac7d is quite short (about 200 base pairs). Thus, the library corresponding to random substitutions of the eleven residues could be obtained by a one-step PCR. This was done using a mixture of three degenerate oligonucleotides (NNS scheme) and three standard oligonucleotides. The codons of the randomized positions were encoded by NNS triplets that allow representation of all amino acids. With this mutagenesis strategy, the theoretical diversity is about $3.2 \cdot 10^{16}$ ($32^{11}$), which exceeds by about four orders of magnitude the experimentally achieved diversity of our library. Indeed, according to the amount of PCR assembly product used to generate the ribosome display construct, the upper estimate of the library was about $3.0 \cdot 10^{12}$ variants. Sequencing of forty random clones confirmed that the observed residue frequency was similar to that predicted (data not shown). The percentage of correct clones, without any frame shifts or deletions, was found to be around 50%. Hence, the "functional" diversity was considered satisfactory and the library was used for selections.

Example 2: Ribosome Display Selections Using Library 11

Three proteins were chosen as targets: DnaK, GarA (both from *Mycobacterium tuberculosis* and the N-terminal domain of PulD (from *Klebsiella oxytoca*). PulD is an outer membrane protein that cannot be maintained in solution without ionic detergents. Therefore, a soluble monomeric fragment was used. This fragment, named PulD-N, corresponds to the N-terminal region of PulD. These targets were chosen because specific and avid binders could be useful tools to study DnaK, GarA and PulD. Furthermore, these proteins are difficult to crystallize for structural studies. Binders recognizing these proteins could be used for co-crystallization trials in the same way as antibody fragments (Ostermeier et al., 1995).

ELISA plates coated with neutravidin were used to immobilize biotinylated proteins and to perform selections. After four rounds of selection, enrichment with specific binders for all three targets was observed (FIG. 6a). In all cases, more than 50% of binding of pools was inhibited with 10 μM of free targets, according to RIAs.

To evaluate pools of binders further by ELISA for the selection with PulD-N, the RT-PCR products from selected pools were cloned into pQE30 vector (Qiagen) using BamHI and HindIII restriction sites. The resulting ligations were used to transform *E. coli* DH5a strain. 96 randomly clones were picked from Petri dish to inoculate a deep-well plate containing 1.5 ml of LB medium per well (100 μg/ml ampicillin, 1% glucose). After overnight culture at 37° C. with shaking at 250 rpm, 0.2 ml of each well from this master plate was used to inoculate an other deep-well plate containing 1.3 ml 2YT medium (100 μg/ml ampicillin) per well. The plate was then incubated at 37° C. for 1 h with shaking (250 rpm). The expression was induced with the addition of 0.5 mM IPTG and incubation at 30° C. for 4 h with shaking (250 rpm). Cells were pelleted with a centrifugation step (2250 g) and supernatants discarded. Proteins were extracted with 50 μl BugBuster (Novagen) per well with shaking at 250 rpm for 30 min, then 250 μl of TBS pH 7.4 (20 mM Tris-HCl, 150 mM NaCl) were added. Cell debris were pelleted with a centrifugation step (2500 g). For ELISA screening, 100 μl of each supernatant were used to test the binding on PulD-N or BSA coated into a Maxisorp plate. The detection was performed using the RGS His antibody HRP conjugate (Qiagen) that detects only the RGS-(His)6-tag from binders and not the (His)6-tag from target proteins and BM-Blue substrate from Roche. All incubation steps were carried-out in TBS pH 7.4 with 0.1% Tween 20. For all clones the OD at 340 nm was measured for PulD-N and BSA binding. Ratio of the value obtained for BSA binding on value for PulD-N was calculated for each clone. A signal to noise ratio superior to 10 was observed for about 92% of clones from round 4 (FIG. 6b). The binding of 6 purified clones from the PulD-N selection (round 4) was tested for DnaK, GarA, PulD-N and BSA by ELISA. As shown in FIG. 6c, the binding was specific for PulD-N. Sequencing of 28 clones from round 4 revealed a high diversity of sequences; indeed no sequence was found more than once, indicating that a higher selection pressure could have been used. Furthermore, no wild type residue could be found at any of all eleven randomized positions (data not shown). The average yield of expression estimated after IMAC (immobilized metal ion affinity chromatography) purification of nine clones was about 70 mg/liter flask culture (4 h induction at 30° C.). The binders could be concentrated at least up to 45 mg/ml. All in all, these observations suggested that the binding area of Sac7d is highly tolerant to substitution and that the selected variants retained satisfactory biophysical properties. However, a more detailed analysis by RIA showed that the average affinity for binders in the pool from round 4 was around 100 nM and a fifth round performed with a mild (2 h) or a more stringent off-rate selection (17 h) failed to increase the average affinity of the anti PulD-N pool (FIG. 7). Such low affinity could be limiting for applications where low nanomolar dissociation constants are required. Hence, the inventors decided to explore other approaches to obtain higher affinity.

Example 3: Design of the Second Generation Libraries (Library 13 and 14)

An intuitive way to improve affinity is to extend the area of binding and thus to increase the potential number of interactions between binders and their ligands. The potential binding area corresponding to randomization of 11 residues had a 890 $Å^2$ solvent-accessible surface. Sac7d being very tolerant to 11 substitutions, it was decided to randomize two or three additional positions: K21 and K22 (library 13) or K21, K22 and T40 (library 14) that correspond to 1130 $Å^2$ and 1200 $Å^2$, respectively. Another explanation could be that the concave binding area is not well-suited to bind protein and, therefore, the use of a flatter surface could improve final affinities. These two new libraries (each of 3.0 $10^{12}$ variants) were constructed the same way as library eleven. Sequencing of seventy random clones from library 14 confirmed that the observed residue frequency was similar to that predicted, with a slight under representation of S, L, and R amino acid residues, while P, N, Q, and H amino acid residues were a bit over represented (data not shown). The percentage of correct clones, without any frame shifts or deletions, was found to be around 65%. Hence, the "functional" diversity was considered satisfactory and the library was used for selections.

Example 4: Ribosome Display Selections with PulD-N as Target Protein, Using Library 13 and 14

Four rounds of selections were performed using these libraries and PulD-N as a target protein. A fifth round was performed in parallel with libraries 11, 13, 14 with a mild off-rate selection for two hours in order to enrich the pools for binders with slower off-rates. A radio immunoassay for the pools after the fifth round (FIG. 7) indicated an enrichment for specific PulD-N binders with the two new libraries. Binding could not be detected on immobilized BSA or neutravidin. Furthermore, this RIA showed that 10 nM of free PulD-N was sufficient to inhibit about 50% of the binding signal with library 13 compared to 100 nM PulD-N for the same level of inhibition with library 11. Library 14 behaved even better, as 1 nM competitor was sufficient to achieve significant inhibition of about 20% of the binding signal. Hence, at least one order of magnitude was gained for the average affinity with the design used for library 14.

Example 5: Characterization of Anti-PulD-N Binders from Library 14

5.1. Sequence Analysis, Expression and Purification of Selected Binders

Since the most promising affinities could be found in the pool obtained from library 14 (round 5), the pool of binders from this library was analyzed. The enriched pool was cloned into the expression plasmid pQE30, and E. coli strain DH5α was used for protein production. Forty-eight individual clones were assayed by an ELISA procedure using immobilized PulD-N or BSA and E. coli crude extracts. For all clones, a significant and specific binding over background was detected. Thus, all binders were sequenced for further analysis.

As observed for library 11, a large diversity of binders remained even after the fifth round of selection (FIG. 8). However, most of the clones could be sorted into six families according to their homologies (data not shown). In addition, two identical clones were found in two cases, all other clones being unique, suggesting a selection convergence. The residues found at randomized positions were of very different nature, with aliphatic and aromatic side-chains as well as charged or hydrophilic side-chains. A clear preference for a particular residue could be observed at some positions. For example, position R42 was occupied by a tyrosine in about half of the clones, probably reflecting its importance for the binding of PulD-N. Among all programmed mutations, no strict conservation of the native residue could be observed, including the three new positions targeted (K21, K22 and T40) compared to library 11 Finally, only seven native residues were retained out of 560 residues in the forty clones sequenced (40×14). Hence, these observations suggest that the 14 positions targeted all tolerate random substitutions.

The binders accumulated in large amounts in the E. coli cytoplasm at 30° C. after overnight growth and could be purified to homogeneity in one single step IMAC with yields up to 200 mg from a one liter shake flask culture (FIG. 9). The proteins ran on a 15% acrylamide SDS-PAGE gel at the position expected for their calculated molecular masses. Purified binders could be concentrated up to 60 mg/ml in a standard TBS buffer with no sign of precipitation and remained soluble over several months at 4° C.

Size-exclusion chromatography showed that clones 6, 39, 40 and 41 binders studied were monomeric. Like Sac7d, all binders appeared larger than predicted in this assay (11.5 kDa determined instead of 9.1 kDa calculated), probably due to a deviation from a truly globular shape caused by the presence of a nine residue N-terminal tag.

5.2. Affinities of PulD-N Binders

In order to identify clones with the highest affinities, forty eight clones were used for micro expressions and IMAC purifications. These purified proteins were then screened by SPR using immobilized biotinylated PulD-N on a streptavidin coated chip. For all assayed binders, no significant binding was observed on the blank surface coated only with steptavidin, supporting the idea that the binding was specific for PulD-N. According to analysis of the dissociation phases, five clones with the slowest off-rates were chosen for detailed affinity determination of the monovalent proteins by SPR.

These five clones, 6, 33, 39, 40 and 41, were further purified by gel filtration. Kinetic analyses were performed at different concentrations and analyzed with a global kinetic fit. The dissociation constants of all PulD-N binders were found to be in the picomolar or low nanomolar range (FIG. 10a and table 3). Clones 6 and 33 had the highest affinities ($K_D$=130 pM and 190 pM, respectively). The association kinetics were slightly reduced (factor 1.3) under high ionic strength conditions (300 mM NaCl), indicating that these associations were not electrostatically assisted (data not shown). $K_D$ values of these five binders were confirmed (FIG. 10b and table 3) by competition SPR analysis (Nieba et al., 1996). A control experiment showed that no binding occurred when testing wild type Sac7d for binding to immobilized PulD-N, indicating that the binding property observed for the selected clones was the result of a newly introduced function and not the result of a pre-existing affinity of Sac7d for PulD-N.

TABLE 3

Summary of dissociation constant determinations by surface plasmon resonance.

| Clone | $k_{on}$ [M$^{-1}$s$^{-1}$] | $k_{off}$ [s$^{-1}$] | $K_D$ [nM][a] | $K_D$ [nM][b] | % acitivity[c] |
|---|---|---|---|---|---|
| 6 | 1.9 10$^7$ | 2.5 10$^{-3}$ | 0.13 | 0.14 ± 0.03 | 90-100 |
| 33 | 1.7 10$^7$ | 3.2 10$^{-3}$ | 0.19 | 0.17 ± 0.03 | 90-100 |
| 39 | 1.7 10$^7$ | 8.6 10$^{-3}$ | 0.52 | 1.1 ± 0.2 | 90-100 |
| 40 | 2.3 10$^7$ | 1.4 10$^{-2}$ | 0.60 | 0.9 ± 0.2 | 90-100 |
| 41 | 2.0 10$^7$ | 1.2 10$^{-2}$ | 0.61 | 1.1 ± 0.1 | 90-100 |

[a]$K_D$ values obtained from kinetic analysis.
[b]$K_D$ values obtained from competition SPR experiments.
[c]from competition SPR experiment analysis.

The sequences analysis of these binders revealed different situations (FIG. 8). The randomized positions in clone 6 and 33 were different, despite the fact that their respective $K_D$ values were in the same range (130-140 pM). In contrast, clone 40 had 11/14 randomized residues in common with those of the clone 41 and had similar $K_D$ values (z 1 nM). Clone 39 shared 10/14 randomized residues with clone 6 but had a 7-fold lower affinity. Interestingly, clone 39 was found to be truncated by 4 residues at its C-terminal end but remained able to bind PulD-N. This is not surprising, as several truncated forms of Sac7d also exist (McAfee et al., 1995).

5.3. Stability of PulD-N Binders

Sac7d is a hyperthemostable protein that unfolds with a $T_m$ of 91° C. at pH 7.0, the thermal stability of the protein decreasing at lower pHs (McCrary et al., 1996). The thermal stabilities of clones 6, 33 and 40 were compared to that of wild type Sac7d by differential scanning calorimetry. In order to insure complete unfolding of the proteins below the high temperature limit of the DSC (125° C.), a pH of 5.6 was used for all scans. The clones were found thermostable with denaturation temperatures between 68° C. and 83° C. (FIG. 11 and table 4). Clone 40 was remarkably stable with a $T_m$ value lower than that of wild-type (89.7° C.) by only 5.8° C., followed by clone 33 ($\Delta T_m$=−10.5° C.), the least stable clone being clone 6 ($\Delta T_m$=−22.0° C.). However, $T_m$ of clone 6 still remains 8° C. above the mean $T_m$ value of proteins of the Protein Data Bank (Freire, 2001). DSC scans were characteristic of cooperative unfolding indicating that, although with a high mutation load (up to 14 residues mutated, i.e. 21% of Sac7d mutated), Sac7d variants were able to adopt a folded structure as for the wild-type. The calorimetric enthalpy (the heat change per mole, $\Delta H_{cal}$) was lower with respect to wild-type (42.5 kcal·mol$^{-1}$) by only 5.8 and 4.8 kcal·mol-1 for clone 40 and clone 33, respectively (table 4). Furthermore, for both clone 40 and clone 33, β, the ratio value of the van't Hoff enthalpy (the heat change per cooperative unfolding unit) to the calorimetric enthalpy was close to one, and close to the β value of wild-type Sac7d. This observation strongly indicated that unfolding of clone 40 and clone 33 corresponded to that of the folded protein monomer (table 4). Clone 6 presented a lower calorimetric enthalpy with respect to wild type (by 18.10 kcal·mol$^{-1}$) and a higher β ratio (table 4). These observations may be related to the partial unfolding of clone 6 protein at acidic pHs where the protein is less stable ($T_m$ of clone 6 is 8° C. higher at pH 7; data not shown). Taken together, these observations show that clones 6, 33 and 40 retained to a large extent the favorable thermal stability of the wild type protein.

TABLE 4

Thermal unfolding parameters for wt and variants Sac7d

| Clone | $T_m$ [° C.][a] | $\Delta H_{cal}$ [$k_{cal} \cdot mol^{-1}$][b] | $\Delta H_{vH}$ [kcal · $mol^{-1}$][b] | $\beta^c$ |
|---|---|---|---|---|
| 6 | 67.7 | 24.4 | 46.3 | 1.9 |
| 33 | 79.2 | 37.7 | 45.2 | 1.2 |
| 40 | 83.9 | 36.7 | 47.7 | 1.3 |
| Sac7d wt | 89.7 | 42.5 | 55.2 | 1.3 |

[a]$T_m$ is ±0.1° C.;
[b]$\Delta H_{cal}$ is ±0.3 $k_{cal} \cdot mol^{-1}$, $\Delta H_{vH}$ is ±0.5 $k_{cal} \cdot mol^{-1}$;
[c]$\beta = \Delta H_{vH}/\Delta H_{cal}$ 5.4. Specificity of PulD-N Binders How specific are these PulD-N binders, and can they be used for biotechnological applications in which specificity is crucial?

To answer these questions, binders 6, 33 and 40 were fused to the N-terminus of E. coli alkaline phosphatase (PhoA). The chimeras (Sac7*-PhoA) were produced as periplasmic proteins in strain DH5α using pQUANTagen vector encoding the PhoA signal peptide. The chimeras were then extracted from the periplasm by osmotic shock and their functionality assayed by ELISA with PulD-N- or BSA-coated wells. Bound fusions were quantified with chromogenic p-nitrophenylphosphate substrate and spectrophotometry (data not shown). A high signal over background was observed for all three chimeras (ratio signal/background>10). This showed that the chimeras were 1) exported in the periplasm, 2) still able to recognize specifically PulD-N and 3) catalytically active. Hence, these fusions could be used as a single step ELISA detection reagent.

To evaluate if these fusions are able to discriminate the PulD-N protein in a complex mixture of proteins, such as in an E. coli crude extract, we used them as a detection reagent for immunoblots. In this experiment, an overnight culture of plasmid-free DH5α was harvested and lysed. The crude extract was aliquoted and decreasing amounts of purified PulD-N were added to each tube. After SDS-PAGE and transfer to a nitrocellulose membrane, PulD-N was detected with the binder-PhoA chimeras in presence of the precipitating chromogenic substrate (NBT/BCIP) in amounts as low as 1.5-3 ng (FIG. 12a) without cross-reactivity. This supported the double functionality of fusions observed with ELISA (FIG. 12a). The detection of low amounts of PulD-N was done while far higher amounts of endogenous proteins were present, demonstrating that the binders 6, 33, and 40 were able to discriminate PulD-N among thousands of proteins and were therefore highly specific.

To evaluate specificity further, binder 6 was covalently immobilized via an amine coupling reaction on a one milliliter NHS-agarose activated column. The soluble fraction of an E. coli crude extract corresponding to 40 ml of a culture producing PulD-N was then injected onto the column. Fractions were collected during loading, washing and elution (acid pH jump) steps. The SDS-PAGE analysis of these fractions showed that the column was able to trap the PulD-N present in the crude extract and that this was done with high specificity, since the only visible band on the stained SDS-PAGE gel corresponded to PulD-N (FIG. 12b). Thus, the ability of the binders to discriminate PulD-N from thousands of proteins was again confirmed.

Example 6: Binding of PulD-N Binders to Dodecameric PulD

Next, the inventors investigated if the three selected Sac7d derivatives with the highest affinities for PulD-N (binders 6, 33 and 40) were able to recognize the full-length PulD protein integrated in to the E. coli outer membrane. Full-length PulD forms dodecamers in the membrane (while PulD-N is monomeric) (Chami et al., 2005) and it could not be excluded that the epitope recognized by each of those binders affected by mutlimerization of PulD, thus preventing their binding to native PulD. When increasing amounts of PulD-containing membranes from E. coli PAP105 (pCHAP3671 pCHAP580) were mixed with saturating amounts of GFP-tagged binders 40 or 33, the amount of binder remaining in the pellets after centrifugation was correspondingly increased (FIG. 13A). The GFP-tagged binders were not sedimented with membranes from PAP105 (pCHAP3711 pCHAP580) containing a PulD variant lacking the N-domain (Guilvout et al., 2006) (FIG. 13A). Thus, binding of these GFP-binder chimeras to membranes is PulD-N-specific, and they bind to the native, dodecameric secretin complex despite the presence of the GFP tag. The binder 6 bound only very weakly to membranes containing PulD (data not shown).

A far-Western immunoblot was used to validate binding of the Sac7d derivatives to PulD dodecamers. All three Sac7*-PhoA chimeras bound specifically to both monomeric and dodecameric PulD but not to PulD-CS (FIG. 13B). Although these three chimeras bound equally well to phenol-dissociated (monomeric; see (Hardie et al., 1996)) PulD (data not shown), they consistently exhibited different apparent affinities for dodecameric PulD, ranging from high (binder 40), to low (binder 6).

Figure 14:
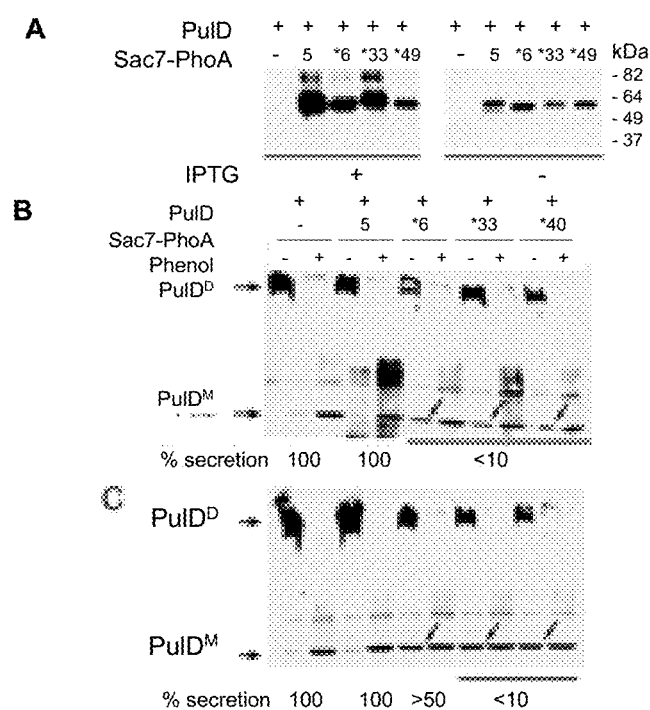

Example 7: PulD-N Binders Inhibit Pullulanase Secretion and Prevent PulD Multimerization Sac7*-PhoA chimeras, in which Sac7d or its derivatives are sandwiched between the PhoA signal peptide and the catalytic part of PhoA, were efficiently exported to the periplasm, as monitored by the high PhoA activity and release upon periplasmic shock. Plasmids encoding the Sac7*-PhoA chimeras were transformed into E. coli strain PAP7232, in which the pul genes are integrated into the chromosome. All three chimeras were produced in similar amounts after IPTG induction and inhibited pullulanase secretion completely, whereas exported Sac7d-PhoA was without effect. Furthermore, neither PulD dodecamers nor monomers were detected in strains producing any of the Sac7*-PhoA chimeras (data not shown). To obtain more-precise information on these phenomena and to study the fate of PulD in strains producing the chimeras, they were produced in envelope protease-deficient strain PAP5198 carrying pCHAP231 (to increase T2SS production; see Guilvout et al., 2006). IPTG-induced levels of Sac7*-PhoA production inhibited pullulanase secretion by >90% (FIG. 14A). Dodecameric PulD was much less abundant, and PulD monomers were correspondingly more abundant (arrows in FIG. 14B) than in controls without chimeras or with Sac7d-PhoA, demonstrating that the chimeras prevent PulD multimerization and cause PulD monomer degradation by envelope proteases. Similar results were obtained with uninduced levels of Sac7*33-PhoA and Sac7*40-PhoA, but substantial pullulanase secretion (>50%) and PulD multimerization occurred when Sac7*6-PhoA was present at uninduced levels (FIG. 14C).

Example 8: Selection of Sac7d Variants Binding to Other Targets

The best library (library 14) was used to obtain binders specific for other targets, by using the same technology as described above.

Selections were carried out by anti-protein ribosome display focusing on the following proteins: PulDN1 (26.8 kDa), NGF (13 kDa), PknG (81.6 kDa), GarA (12 kDa) and lysozyme (14.3 kDa) up to cycle No. 5. During the $4^{th}$ cycle, the selection process was conducted in parallel, with and without the target. FIG. 15 shows that, after 4 selection cycles, a PCR product is obtained only when the target is present (lanes marked as "+"). This suggests that the selection pools were enriched with clones specific for each of the targets tested.

In order to further evaluate the success of the selection process, a competitive radio immuno assay (RIA) was carried out using the target proteins at various inhibitory concentrations. These RIAs clearly show that there is marked enrichment for anti-PknG, anti-lysozyme and anti-PulDN1 selections whereas in the case of NGF and GarA, the results suggest that the selection has not yet sufficiently converged. FIG. 16 shows that the average anticipated affinity for the anti-PknG and anti-lysozyme variants is of the order of 1 to 10 nM.

The anti-lysozyme, anti-PknG and anti-GarA selection pools used in cycle No. 5 were screened according to the ELISA method by preparing 96-well micro-cultures and using bacterial lysis supernatants after inducing clone expression with IPTG for 4 hours at 30° C. The results presented in FIG. 17 clearly show that there are specific clones for each of the targets. Although the RIA for GarA was not encouraging, a significant proportion of positive clones were nevertheless detected with the ELISA method. A particular clone binding GarA was isolated and sequenced. FIG. 19 shows the alignment of this binder's sequence (GSVKVKFLYLGEEKEVDTSKIWFVM-RAGKHVYFQYDDNGKYGIGWVREKDAPKEL LDM-LARAEREKKL, SEQ ID No: 47) with Sac7d.

As regards PknG, a significant proportion of clones appear to bind to BSA, which suggests that an additional selection cycle is required in order to eliminate them. Anti-PulDN1 and anti-NGF screenings are carried out.

The positive anti-lysozyme clones were screened and classed by Biacore for the best anticipated affinities (long complex dissociation time ($k_{off}$)), by preparing 96-well microcultures. The 24 best clones selected were then sequenced (FIG. 18). A preferential sequence, such as that of the Lys_B11 clone, is clearly evident since it is represented several times (although encoded for certain positions by different codons for the same amino acid). The screening of cycle No. 4 revealed a greater diversity (not shown).

Three clones of different sequences (Lys_B3, Lys_H4 and Lys_H8) were produced in *E. coli*, purified on a large scale by IMAC and then passed through a molecular sieve. The production levels obtained were approximately 120, 40 and 25 mg/L of culture, respectively. The affinities determined by Biacore are being obtained and processed. Current (preliminary) data indicate affinities of the order of 15 nM, 3 nM and 25 nM (Lys_B3, Lys_H4 and Lys_H8, respectively).

The three anti-lysozyme clones (Lys_B3, Lys_H4 and Lys_H8) are currently being characterised by microcalorimetry in order to determine their thermostabilities and affinities in solution.

The clones obtained from other selections will also be screened by Biacore and sequenced, and the affinities of certain clones will be determined more precisely by Biacore.

Example 9: Selection of Sac7d Variants Binding to a Human IgG Fc Fragment 9.1. Selection of Fc Binders A Human IgG Fc fragment (MW=50 kDa) provided by Bio-Rad was chemically biotinylated using sulfosuccinimidyl-6-(biotinamido) hexanoate. The degree of biotinylation, determined by a HABA assay, was about 2 to 3 molecules of biotin per protein molecule. Biotinylated Fc was bound to immobilized neutravidin or streptavidin in a Maxisorp plate (Nunc) and selections by ribosome display were performed at 4° C. using the library derived from Sac7d (as described above). Four rounds of selection were performed to isolate binders. Neutravidin and streptavidin were used alternatively from round to round to avoid unspecific binders.

9.2. Evaluation of the Pool of Sequences Selected

After a round of selection, a pool of sequences (supposedly binders) carrying an RGS-His6-tag was obtained. This pool was translated in vitro using an *E. coli* S30 extract, and its binding activity wad tested by ELISA using an anti-RGS-His6-tag-HRP conjugate. A binding activity was detected in the pool of selection against passively immobilized Fc fragment, and no binding signal was observed against BSA, Neutravidin and Streptavidin (not shown). This result suggests that the pool of binders is probably specific of Fc fragment and that there is no significant contribution of Neutravidin or Streptavidin to binding activity.

A competition ELISA with this translated pool was also carried-out to roughly evaluate the average affinity of selected binders. In this experiment, the translation was pre-incubated with several concentrations of Fc fragment before incubation in the ELISA plate in which Fc fragment was immobilized. As shown in FIG. 20, 20% and 70% of the signal could be inhibited with 10 nM and 100 nM Fc, respectively. This result suggests that expected average affinity is around dozens of nM. This range of affinity is similar to what was observed for PulD-N selection.

Example 10: Automation of the Technology

To increase the potential of the above-described technology, the ribosome display selection protocol (FIG. 21) is transferred to an automated platform for the subsequent, simultaneous and rapid testing of numerous targets (still using library 14, or any other library, for example starting from an OB-fold protein different from Sac7d).

A Tecan Gemini 150 robot has been fully equipped to this aim. This station comprises: several heating/cooling/agitating blocks, a MJ research thermocycler for automated station with motorized lid, all the needed accessories to perform reaction set-ups, RNA and DNA cleanups as well as to measure concentrations of nucleic acids with an integrated microplate reader. The goal is to achieve one round of selection without manual intervention at all. Manual intervention would only be required between the rounds of selection as many plastic ware have to be replaced at the end of a cycle. Manual selections by ribosome display (FIG. 21) are repetitive (five rounds necessary to enrich for binders), fastidious (many steps of transcription, translation, PCR, RT-PCR) and therefore time consuming for few targets, or even not manageable for more than four targets by one experimentalist. Hence, there is a great practical advantage to perform selections using a robot. After validation of the selection protocol on the robotic station (with PulD target), it is possible to select binders against up to 48 targets on a time scale of one or two weeks.

Discussion

The inventors explored potential benefits of what evolution has accomplished with OB-folds during millions of years to adapt this fold to bind a wide diversity of ligands: metallic ions, sugars, nucleic acids (RNA, single and double stranded DNA) and proteins. They were able to show that a member of the OB-fold family can indeed be converted from DNA recognition to protein recognition by in vitro evolution. This led successfully to the generation of high affinity, high-specificity binders for a given target.

Design of Sac7d Libraries

Figure 2:
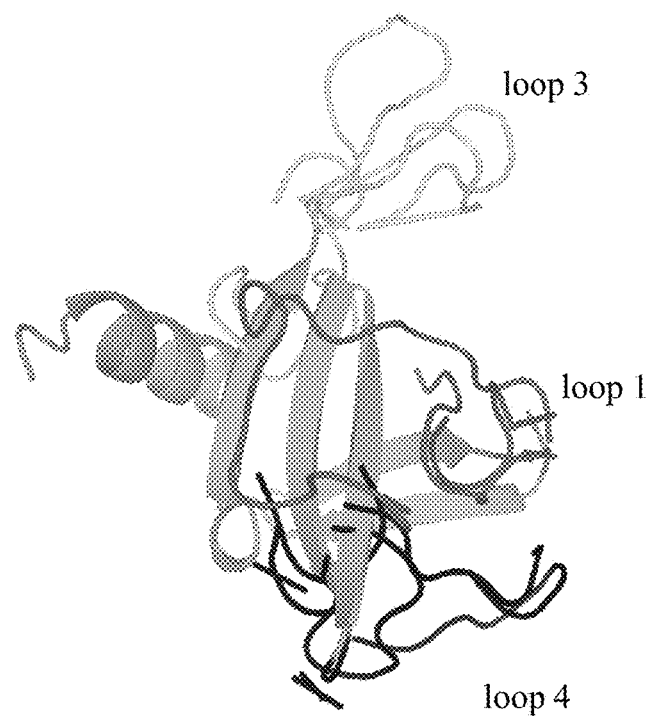
FIG. 2: Schematic representation of loops 1, 3 and 4 of various OB-fold domains. The RSCB PBD structure files used for performing this superimposition are the following:_1azp (i.e., Sac7d), 1tvxA, 1dokA, 1bqq, 1csp, 3seb, 1br9, 2bosA, 1bf4A and 1quqB. For clarity of the figure, only the structure of Sac7d is represented.

The observation that the OB-fold architecture is polarized, meaning that the binding face is always the same in all OB-fold proteins (Arcus, 2002), enabled the design of libraries of Sac7d variants retaining the favorable biophysical properties of the wild type protein. Different OB-fold proteins can exhibit substantial variation in the lengths of loops 1, 3 and 4 (FIGS. 1b and 2), which are often implicated in ligand binding. Although most scaffolds used up to now are based on randomization of flexible loops similarly to those in antibodies (Binz et al., 2005), the inventors decided to keep the original loop lengths from the native Sac7d protein. They first postulated that the lightly concave part of the binding area would be best adapted to globular shape of proteins used as targets. However, as reported above, the randomization of the residues from this area did not allow to obtain better than high nanomolar binders. This potential binding surface corresponds to a solvent-accessible surface area to of about 890 Å$^2$ and is in the typical range for antibody-protein associations (777±135 Å$^2$) (Jones and Thornton, 1996). Thus, this surface should be sufficient to provide enough energy of interaction to get monomeric binders with high affinity. The extension of the potential binding area with three more substitutions was then tested.

Selection with Sac7d Libraries

Selections of binders against several different targets were successfully carried out using ribosome display. In contrast to selections with fully synthetic naïve scFv libraries, for which 5 to 6 rounds were necessary for enrichment (Hanes et al., 2000), a significant enrichment was observed already after the third round with Sac7d libraries. This could be explained by a more efficient folding of Sac7d compared to antibodies, as it requires neither disulfide bond formation to reach its native state nor the correct association of two linked structural domains (as for scFv fragments) to be functional. The high rate of enrichment is similar to that described for the DARPin scaffold (Binz et al., 2004a). Finally, outputs of selections against PulD-N demonstrate that the libraries contain sufficient functional diversity to provide different binders able to recognize a same target protein. This validated the design of Sac7d libraries according to the invention.

Properties of Selected Binders

Characterization of the selected monomeric binders against PulD-N showed that picomolar affinities can be obtained with Sac7d libraries. These affinities are among the highest obtained with a scaffold protein without the need for an affinity maturation step (for a review, see (Hosse et al., 2006) and references therein). The kinetics of bindings were also remarkable, with rates of association around 2 10$^7$ M$^{-1}$·s$^{-1}$ that rank PulD-N binders in the upper range of diffusion-limited association rates for protein-protein interactions (Gabdoulline and Wade, 1997). The rates of association do not appear to be electrostatically assisted. Thus, the high rates of association could be explained by the "preformed" shape of the binder that matches geometrically to the target without requiring conformational changes.

The high affinities obtained are associated with a very high specificity. The inventors have shown that whatever the context (E. coli crude extract or membranes) and the approach (immunoblot or affinity chromatography), all tested binders were able to discriminate the target among thousands of other proteins. This stringent specificity could be related to the rigidity of the scaffold that prevents slight adaptations to different targets. Furthermore, all of the dozens of binders screened were shown to be target-specific in ELISA assays, indicating that the selection pressure applied was sufficient to get rid of sticky molecules.

Recombinant protein yields for variants (up to 200 mg/l E. coli culture) were much higher than reported for Sac7d (about 10-15 mg/l). This difference can be explained by the lysis that occurs few hours after induction of the expression of the wild-type sac7d gene. This toxicity is probably due to perturbations of regulation pathways induced by Sac7d binding to the E. coli genome, as Sac7d is a general DNA binding protein. This limitation is not seen for variants, suggesting that variants had indeed lost their DNA binding property.

The thermodynamic stability observed for three variants compares well with several other proteins from thermophiles (Kahsai et al., 2005) and the thermal stability of the binders remained close to that of wild-type Sac7d. Clone 6, the least stable clone analyzed, still remained a thermostable protein with a $T_m$ of about 68° C. at pH 5.6, a $T_m$ by 8° C. lower compared to that at pH 7.0. Hence, it appears that despite the variable $T_m$ values observed from clone to clone, globally the library design described above, combined with the use of a protein of an extremophile origin, led to the generation of very stable proteins with the desired recognition properties.

Binding In Vivo and Intracellular Inhibition of Pullulanase Secretion

All three Sac7*-PhoA chimeras that were tested bound to monomeric full-length PulD. Sac7*40-PhoA and Sac7*33-PhoA bound well to dodecameric PulD, indicating that their epitopes remain accessible. In contrast, Sac7*6-PhoA bound only weakly to PulD dodecamers but had the highest affinity for PulD-N in vitro, indicating that its epitope is partially masked upon multimerization and is different from those recognized by Sac7*40 and Sac7*33. ITC competition experiments indicated that epitopes recognized by Sac7*6 and Sac7*40 are identical or overlap (data not shown). The differences in the in vivo effects of these two binders, when fused to PhoA, suggest that their epitopes overlap.

All three Sac7*-PhoA variants prevented PulD multimerization and targeted the PulD monomers for degradation by envelope proteases, thereby blocking pullulanase secretion. Earlier evidence indicated that the N domain does not influence PulD multimerization (Guilvout et al., 2006). PhoA dimerization in Sac7*-PhoA might cause steric hindrance and consequent mispositioning of PulD monomers. Secretion levels in strains producing Sac7*-PhoA remained very low when the level of PulD produced was increased and envelope proteases were inactivated (FIG. 14B). Low secretion could be due to the presence of only a few PulD dodecamers, channel occlusion, or masking of an essential interaction site with substrate (Shevchik et al., 1997) or another secretion component (Possot et al., 2000) by bound chimeras.

Reducing the level of Sac7*33 or Sac7*40 (by eliminating induction by IPTG) did not diminish their effect on secretion or PulD multimerization, but Sac7*6-PhoA was almost without effect under these conditions (FIG. 14C), even though it was at least as abundant as the other chimeras (FIG. 14A). Two different scenarios could explain this observation. First, the highly abundant Sac7*6-PhoA binds to almost all PulD monomers and prevents their multimerization. However, when Sac7*6-PhoA levels are lower, it cannot compete efficiently with PulD monomer-monomer interactions, and enough multimers assemble to allow efficient secretion. The apparently lower affinity of Sac7*6-PhoA for dodecameric PulD is insufficient to prevent secretion. Second, binding of the chaperone PulS to PulD monomers, a prerequisite for their correct targeting to the outer membrane (Guilvout et al., 2006; Hardie et al., 1996), prevents Sac7*6-PhoA binding and permits correct multimerization. In this scenario, the outcome depends on which protein binds first to PulD, PulS or Sac7*6-PhoA. Both scenarios are in agreement with the fact that the epitope recognized by Sac7*6 is strongly masked upon PulD multimerization, suggesting that it is at the interface between two monomers.

Potential Biotechnological Applications

These binders retained most of the very favorable biophysical properties required in an alternative scaffold to antibodies. Their properties compare well with previously proposed alternatives to antibodies such as affibodies (Nord et al., 1997), fibronectin (Xu et al., 2002), or ankyrins (Binz et al., 2004a). Indeed, they are very well expressed in E. coli (in the cytoplasm or the periplasm), stable, soluble, able to recognize a protein target with a high affinity and a high specificity, and they can be fused functionally to different reporter proteins (PhoA and GFP). In other words, they are cheap to produce, easy to purify and to handle. This opens the door for a number of biotechnological applications.

Furthermore their very small size, three or nineteen times smaller than a scFv or an IgG, respectively, makes them ideal candidates for the design of chimeric proteins in which binding modules are needed while maintaining a reasonable size. It is also conceivable to link several binders with different specificities and, thus, to construct fusions with multiple specificities. Another advantage of small binders such as Sac7d is their potential ability to bind buried epitopes that are sterically inaccessible to natural antibodies or their fragments.

It can be noted that the capacity of the binders to bind to target proteins is not limited to targets with a high molecular weight. Indeed, the results already obtained, in addition to those concerning PulD, show that the bank developed from Sac7d has allowed the isolation of clones specifically binding to three new targets, which cover a wide range of molecular weights (Lysozyme=14.3 kDa, GarA=17.3 kDa, PknG=81.6 kDa). The expression of these binders in E. coli is far superior to the levels observed for recombinant antibody fragments. The affinities obtained are of the order of nM without selection based on long kw values (off-rate selection), due to a shortage of time. This selection step is needed in order to obtain sub-nanomolar affinities, and is currently performed.

To address how specific could be PulD binders, the inventors have already demonstrated they could be used for the development of detection reagents. For example, one step ELISA or Western blots are achievable by fusion of binders to alkaline phosphatase. Another example is the use of GFP fusions for in vitro detection that paves the way to in vivo intracellular localization. It was also demonstrated that affinity chromatography can be performed with these binders and that a protein can be purified to homogeneity by single step purification. Other applications could use these binders, such as protein chip arrays, biosensors or switchables in vivo knock out for example.

CONCLUSIONS

The strategy to use an OB-fold protein to get binders able to recognize target proteins with high affinity and very fine specificity was successfully validated by the above results. The starting point was Sac7d, a general DNA binding protein. Sac7d and its derivates are now able to recognize two structurally unrelated families of ligands: DNA and proteins. Hence, the inventors have reproduced in vitro the binding adaptation of an OB-fold for a given target, such as Nature as already achieved. It is therefore conceivable, that Sac7d might also be adapted to other known ligands of OB-fold proteins, such as single strand DNA, RNA or sugars. In addition to their potential use in functional knock-out experiments, these binders could be used for affinity chromatography, detection, in vivo localization experiments, etc. Indeed, the favorable biophysical properties of these binders, along with their facile fusion to different reporter proteins and their small size (3 and 19 times smaller than scFv and IgG, respectively), might facilitate these applications.

REFERENCES

Agback, P., Baumann, H., Knapp, S., Ladenstein, R., and Hard, T. (1998). Architecture of nonspecific protein-DNA interactions in the Sso7d-DNA complex. Nat Struct Biol 5, 579-584.

Arcus, V. (2002). OB-fold domains: a snapshot of the evolution of sequence, structure and function. Curr Opin Struct Biol 12, 794-801.

Berman, H. M., Westbrook, J., Feng, Z., Gilliland, G., Bhat, T. N., Weissig, H., Shindyalov, I. N., and Bourne, P. E. (2000). The Protein Data Bank. Nucleic Acids Res 28, 235-242.

Binz, H. K., Amstutz, P., Kohl, A., Stumpp, M. T., Briand, C., Forrer, P., Grutter, M. G., and Pluckthun, A. (2004a). High-affinity binders selected from designed ankyrin repeat protein libraries. Nat Biotechnol 22, 575-582.

Binz, H. K., Amstutz, P., Kohl, A., Stumpp, M. T., Briand, C., Forrer, P., Grutter, M. G., and Pluckthun, A. (2004b). High-affinity binders selected from designed ankyrin repeat protein libraries. Nat Biotechnol 22, 575-582. Epub 24 Apr. 2018.

Binz, H. K., Amstutz, P., and Pluckthun, A. (2005). Engineering novel binding proteins from nonimmunoglobulin domains. Nat Biotechnol 23, 1257-1268.

Boder, E. T., and Wittrup, K. D. (1997). Yeast surface display for screening combinatorial polypeptide libraries. Nat Biotechnol 15, 553-557.

Chami, M., Guilvout, I., Gregorini, M., Remigy, H. W., Muller, S. A., Valerio, M., Engel, A., Pugsley, A. P., and Bayan, N. (2005). Structural insights into the secretin PulD and its trypsin-resistant core. J Biol Chem 280, 37732-37741.

Daefler, S., Guilvout, I., Hardie, K. R., Pugsley, A. P., and Russel, M. (1997). The C-terminal domain of the secretin PulD contains the binding site for its cognate chaperone, PulS, and confers PulS dependence on pIVfl function. Mol Microbiol 24, 465-475.

d'Enfert, C., Chapon, C., and Pugsley, A. P. (1987). Export and secretion of the lipoprotein pullulanase by *Klebsiella pneumoniae*. Mol Microbiol 1, 107-116.

d'Enfert, C., Reyss, I., Wandersman, C., and Pugsley, A. P. (1989). Protein secretion by gram-negative bacteria. Characterization of two membrane proteins required for pullulanase secretion by *Escherichia coli* K-12. J Biol Chem 264, 17462-17468.

Edmondson, S. P., and Shriver, J. W. (2001). DNA binding proteins Sac7d and Sso7d from *Sulfolobus*. Methods Enzymol 334, 129-145.

Freire, E. (2001). The thermodynamic linkage between protein structure, stability, and function. Methods Mol Biol 168, 37-68.

Gabdoulline, R. R., and Wade, R. C. (1997). Simulation of the diffusional association of barnase and barstar. Biophys J 72, 1917-1929.

Gao, Y. G., Su, S. Y., Robinson, H., Padmanabhan, S., Lim, L., McCrary, B. S., Edmondson, S. P., Shriver, J. W., and Wang, A. H. (1998). The crystal structure of the hyperthermophile chromosomal protein Sso7d bound to DNA. Nat Struct Biol 5, 782-786.

Georgiou, G., Stathopoulos, C., Daugherty, P. S., Nayak, A. R., Iverson, B. L., and Curtiss, R., 3rd (1997). Display of heterologous proteins on the surface of microorganisms: from the screening of combinatorial libraries to live recombinant vaccines. Nat Biotechnol 15, 29-34.

Guilvout, I., Chami, M., Engel, A., Pugsley, A. P., and Bayan, N. (2006). Bacterial outer membrane secretin PulD assembles and inserts into the inner membrane in the absence of its pilotin. Embo J 25, 5241-5249.

Guilvout, I., Hardie, K. R., Sauvonnet, N., and Pugsley, A. P. (1999). Genetic dissection of the outer membrane secretin PulD: are there distinct domains for multimerization and secretion specificity? J Bacteriol 181, 7212-7220.

Hanes, J., Jermutus, L., Weber-Bornhauser, S., Bosshard, H. R., and Pluckthun, A. (1998). Ribosome display efficiently selects and evolves high-affinity antibodies in vitro from immune libraries. Proc Natl Acad Sci USA 95, 14130-14135.

Hanes, J., and Pluckthun, A. (1997). In vitro selection and evolution of functional proteins by using ribosome display. Proc Natl Acad Sci USA 94, 4937-4942.

Hanes, J., Schaffitzel, C., Knappik, A., and Pluckthun, A. (2000). Picomolar affinity antibodies from a fully synthetic naive library selected and evolved by ribosome display. Nat Biotechnol 18, 1287-1292.

Hardie, K. R., Lory, S., and Pugsley, A. P. (1996). Insertion of an outer membrane protein in *Escherichia coli* requires a chaperone-like protein. Embo J 15, 978-988.

He, M., and Taussig, M. J. (2002). Ribosome display: cell-free protein display technology. Brief Funct Genomic Proteomic 1, 204-212.

Hible, G., Renault, L., Schaeffer, F., Christova, P., Zoe Radulescu, A., Evrin, C., Gilles, A. M., and Cherfils, J. (2005). calorimetric and crystallographic analysis of the oligomeric structure of *Escherichia coli* GMP kinase. J Mol Biol 352, 1044-1059.

Holm, L., and Park, J. (2000). DaliLite workbench for protein structure comparison. Bioinformatics 16, 566-567.

Holm, L., and Sander, C. (1998). Touring protein fold space with Dali/FSSP. Nucleic Acids Res 26, 316-319.

Hosse, R. J., Rothe, A., and Power, B. E. (2006). A new generation of protein display scaffolds for molecular recognition. Protein Sci 15, 14-27.

Jermutus, L., Honegger, A., Schwesinger, F., Hanes, J., and Pluckthun, A. (2001). Tailoring in vitro evolution for protein affinity or stability. Proc Natl Acad Sci USA 98, 75-80.

Jones, S., and Thornton, J. M. (1996). Principles of protein-protein interactions. Proc Natl Acad Sci USA 93, 13-20.

Kahsai, M. A., Martin, E., Edmondson, S. P., and Shriver, J. W. (2005). Stability and flexibility in the structure of the hyperthermophile DNA-binding protein Sac7d. Biochemistry 44, 13500-13509.

Kitov, P. I., Sadowska, J. M., Mulvey, G., Armstrong, G. D., Ling, H., Pannu, N. S., Read, R. J., and Bundle, D. R. (2000). Shiga-like toxins are neutralized by tailored multivalent carbohydrate ligands. Nature 403, 669-672.

Kloks, C. P., Spronk, C. A., Lasonder, E., Hoffmann, A., Vuister, G. W., Grzesiek, S., and Hilbers, C. W. (2002). The solution structure and DNA-binding properties of the cold-shock domain of the human Y-box protein YB-1. J Mol Biol 316, 317-326.

Lopez, R., Silventoinen, V., Robinson, S., Kibria, A., and Gish, W. (2003). WU-Blast2 server at the European Bioinformatics Institute. Nucleic Acids Res 31, 3795-3798.

Mathonet, P., and Fastrez, J. (2004). Engineering of non-natural receptors. Curr Opin Struct Biol 14, 505-511.

McAfee, J. G., Edmondson, S. P., Datta, P. K., Shriver, J. W., and Gupta, R. (1995). Gene cloning, expression, and characterization of the Sac7 proteins from the hyperthermophile *Sulfolobus acidocaldarius*. Biochemistry 34, 10063-10077.

McCrary, B. S., Edmondson, S. P., and Shriver, J. W. (1996). Hyperthermophile protein folding thermodynamics: differential scanning calorimetry and chemical denaturation of Sac7d. J Mol Biol 264, 784-805.

Mitton-Fry, R. M., Anderson, E. M., Hughes, T. R., Lundblad, V., and Wuttke, D. S. (2002). Conserved structure for single-stranded telomeric DNA recognition. Science 296, 145-147.

Murzin, A. G. (1993). OB(oligonucleotide/oligosaccharide binding)-fold: common structural and functional solution for non-homologous sequences. Embo J 12, 861-867.

Nieba, L., Krebber, A., and Pluckthun, A. (1996). Competition BIAcore for measuring true affinities: large differences from values determined from binding kinetics. Anal Biochem 234, 155-165.

Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.

Notredame, C., Higgins, D. G., and Heringa, J. (2000). T-Coffee: A novel method for fast and accurate multiple sequence alignment. J Mol Biol 302, 205-217.

Ostermeier, C., Iwata, S., Ludwig, B., and Michel, H. (1995). Fv fragment-mediated crystallization of the membrane protein bacterial cytochrome c oxidase. Nat Struct Biol 2, 842-846.

Papageorgiou, A. C., Tranter, H. S., and Acharya, K. R. (1998). Crystal structure of microbial superantigen staphylococcal enterotoxin B at 1.5 A resolution: implications for superantigen recognition by MHC class II molecules and T-cell receptors. J Mol Biol 277, 61-79.

Pearl, F. M., Bennett, C. F., Bray, J. E., Harrison, A. P., Martin, N., Shepherd, A., Sillitoe, I., Thornton, J., and Orengo, C. A. (2003). The CATH database: an extended protein family resource for structural and functional genomics. Nucleic Acids Res 31, 452-455.

Plotnikov, V. V., Brandts, J. M., Lin, L. N., and Brandts, J. F. (1997). A new ultrasensitive scanning calorimeter. Anal Biochem 250, 237-244.

Possot, O. M., Vignon, G., Bomchil, N., Ebel, F., and Pugsley, A. P. (2000). Multiple interactions between pullulanase secreton components involved in stabilization and cytoplasmic membrane association of PulE. J Bacteriol 182, 2142-2152.

Qian, J., Stenger, B., Wilson, C. A., Lin, J., Jansen, R., Teichmann, S. A., Park, J., Krebs, W. G., Yu, H., Alexandrov, V., et al. (2001). PartsList: a web-based system for dynamically ranking protein folds based on disparate attributes, including whole-genome expression and interaction information. Nucleic Acids Res 29, 1750-1764.

Robinson, H., Gao, Y. G., McCrary, B. S., Edmondson, S. P., Shriver, J. W., and
Wang, A. H. (1998). The hyperthermophile chromosomal protein Sac7d sharply kinks DNA. Nature 392, 202-205.

Roussel, A., Anderson, B. F., Baker, H. M., Fraser, J. D., and Baker, E. N. (1997). Crystal structure of the streptococcal superantigen SPE-C: dimerization and zinc binding suggest a novel mode of interaction with MHC class II molecules. Nat Struct Biol 4, 635-643.

Samygina, V. R., Popov, A. N., Rodina, E. V., Vorobyeva, N. N., Lamzin, V. S., Polyakov, K. M., Kurilova, S. A., Nazarova, T. I., and Avaeva, S. M. (2001). The structures of Escherichia coli inorganic pyrophosphatase complexed with Ca(2+) or CaPP(i) at atomic resolution and their mechanistic implications. J Mol Biol 314, 633-645.

Schaffitzel, C., Hanes, J., Jermutus, L., and Pluckthun, A. (1999). Ribosome display: an in vitro method for selection and evolution of antibodies from libraries. J Immunol Methods 231, 119-135.

Shevchik, V. E., Robert-Baudouy, J., and Condemine, G. (1997). Specific interaction between OutD, an Erwinia chrysanthemi outer membrane protein of the general secretory pathway, and secreted proteins. Embo J 16, 3007-3016.

Smith, G. P. (1985). Filamentous fusion phage: novel expression vectors that display cloned antigens on the virion surface. Science 228, 1315-1317.

Su, S., Gao, Y. G., Robinson, H., Liaw, Y. C., Edmondson, S. P., Shriver, J. W., and Wang, A. H. (2000). Crystal structures of the chromosomal proteins Sso7d/Sac7d bound to DNA containing T-G mismatched base-pairs. J Mol Biol 303, 395-403.

Wilson, D. S., Keefe, A. D., and Szostak, J. W. (2001). The use of mRNA display to select high-affinity protein-binding peptides. Proc Natl Acad Sci USA 98, 3750-3755.

Xu, L., Aha, P., Gu, K., Kuimelis, R. G., Kurz, M., Lam, T., Lim, A. C., Liu, H., Lohse, P. A., Sun, L., et al. (2002). Directed evolution of high-affinity antibody mimics using mRNA display. Chem Biol 9, 933-942.

The invention claimed is:

1. A combinatorial library of variants of a starting OB-fold protein in which 5 to 31 residues involved in the binding of said starting OB-fold protein with its native ligand have been randomized, wherein said starting OB-fold protein is selected from the group consisting Sac7d or Sac7e from *Sulfolobus acidocaldarius*, Sso7d, from *Sulfolobus solfataricus*, DBP 7 from *Sulfolobus tokodaii*, Ssh7b from *Sulfolobus shibatae*, Ssh7a from *Sulfolobus shibatae*, and p7ss from *Sulfolobus solfataricus*, and wherein said residues that are randomized in said variants are selected amongst the residues corresponding to V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51 of Sac7d.

2. The combinatorial library of variants of claim 1, wherein 11, 12, 13, 14, 15, 16, 17 or 18 residues are randomized, chosen amongst residues corresponding to K7, Y8, K9, K21, K22, W24, V26, K28, M29, S31, T33, K39, T40, R42, A44, S46, E47 and K48 of Sac7d.

3. The combinatorial library of variants of claim 1, wherein 11, 12, 13, 14, 15 or 16 residues are randomized, chosen amongst residues corresponding to K7, Y8, K9, K21, K22, W24, V26, K28, M29, S31, T33, K39, T40, R42, A44 and S46 of Sac7d.

4. The combinatorial library of variants of claim 1, in which the randomized residues in said variants comprise at least the residues corresponding to K7, Y8, K9, W24, V26, M29, S31, T33, R42, A44 and S46 of Sac7d.

5. The combinatorial library of variants of claim 1, wherein only residues corresponding to K7, Y8, K9, W24, V26, M29, S31, T33, R42, A44 and S46 of Sac7d are randomized in said variants.

6. The combinatorial library of variants of claim 1, wherein residues corresponding to K7, Y8, K9, W24, V26, M29, S31, T33, R42, A44 and S46 of Sac7d are randomized in said variants and, in which one, two or three additional residues selected amongst residues corresponding to K21, K22 and T40 of Sac7d are also randomized in said variants.

7. The combinatorial library of variants of claim 1, wherein residues corresponding to K7, Y8, K9, K21, K22, W24, V26, M29, S31, T33, R42, A44 and S46 of Sac7d are randomized in said variants.

8. The combinatorial library of variants of claim 1, wherein 1 to 15 random amino acid residues are inserted in the region corresponding to the amino acids in position 25 to 30 of Sac7d, and/or 1 to 15 random amino acid residues are inserted in the region corresponding to the amino acids in position 35 to 40 of Sac7d, and/or 1 to 20 random amino acid residues are inserted in the region corresponding to the amino acids in position 7 to 12 of Sac7d in said variants.

9. The combinatorial library of variants of claim 1, wherein 1 to 4 amino acid residues selected amongst residues corresponding to A59, R60, A61 and E64 of Sac7d are deleted in said variants.

10. The combinatorial library of variants of claim 1, wherein the starting OB fold protein is Sac7d or Sso7d and 8 to 16 residues that are randomized in said variants.

11. A method for obtaining a combinatorial library of variants of a starting OB-fold protein, comprising the step of randomizing 5 to 31 residues involved in the binding of said starting OB-fold protein with its native ligand, and recovering the variants thereby obtained, wherein said starting OB-fold protein is selected from the group consisting Sac7d or Sac7e from *Sulfolobus acidocaldarius*, Sso7d, from *Sulfolobus solfataricus*, DBP 7 from *Sulfolobus tokodaii*, Ssh7b from *Sulfolobus shibatae*, Ssh7a from *Sulfolobus shibatae*, and p7ss from *Sulfolobus solfataricus*, and wherein said residues that are randomized in said variants are selected amongst the residues corresponding to V2, K3, K5, K7, Y8, K9, G10, E14, T17, K21, K22, W24, V26, G27, K28, M29, S31, T33, D36, N37, G38, K39, T40, R42, A44, S46, E47, K48, D49, A50 and P51 of Sac7d.

12. The method of claim 11, wherein 11, 12, 13, 14, 15, 16, 17 or 18 residues are randomized, chosen amongst residues corresponding to K7, Y8, K9, K21, K22, W24, V26, K28, M29, S31, T33, K39, T40, R42, A44, S46, E47 and K48 of Sac7d.

13. The method of claim 11, wherein 11, 12, 13, 14, 15 or 16 residues are randomized, chosen amongst residues corresponding to K7, Y8, K9, K21, K22, W24, V26, K28, M29, S31, T33, K39, T40, R42, A44 and S46 of Sac7d.

14. The method of claim 11, in which the randomized residues in said starting OB-fold protein comprise at least the residues corresponding to K7, Y8, K9, W24, V26, M29, S31, T33, R42, A44 and S46 of Sac7d.

15. The method of claim 11, wherein only residues corresponding to K7, Y8, K9, W24, V26, M29, S31, T33, R42, A44 and S46 of Sac7d are randomized in said starting OB-fold protein.

16. The method of claim 11, wherein residues corresponding to K7, Y8, K9, W24, V26, M29, S31, T33, R42, A44 and S46 of Sac7d are randomized in said starting OB-fold protein and, in which one, two or three additional residues selected amongst residues corresponding to K21, K22 and T40 of Sac7d are also randomized in said starting OB-fold protein.

17. The method of claim 11, wherein residues corresponding to K7, Y8, K9, K21, K22, W24, V26, M29, S31, T33, R42, A44 and S46 of Sac7d are randomized in said starting OB-fold protein.

18. The method of claim 11, wherein 1 to 15 random amino acid residues are inserted in the region corresponding to the amino acids in position 25 to 30 of Sac7d, and/or 1 to 15 random amino acid residues are inserted in the region corresponding to the amino acids in position 35 to 40 of Sac7d, and/or 1 to 20 random amino acid residues are inserted in the region corresponding to the amino acids in position 7 to 12 of Sac7d in said starting OB-fold protein.

19. The method of claim 11, wherein 1 to 4 amino acid residues selected amongst residues corresponding to A59, R60, A61 and E64 of Sac7d are deleted in said starting OB-fold protein.

20. The method of claim 11, wherein the starting OB fold protein is Sac7d or Sso7d and 8 to 16 residues that are randomized in said variants.

* * * * *

SEQUENCE LISTING

```
<160> NUMBER OF SEQ ID NOS: 67

<210> SEQ ID NO 1
<211> LENGTH: 66
<212> TYPE: PRT
<213> ORGANISM: Sulfolobus sp.

<400> SEQUENCE: 1

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65

<210> SEQ ID NO 2
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 6
<220> FEATURE:
<221> NAME/KEY: DOMAIN
<222> LOCATION: (1)..(12)
<223> OTHER INFORMATION: MRGS-(His)6-tag

<400> SEQUENCE: 2

Met Arg Gly Ser His His His His His His Gly Ser Val Lys Val Lys
```

```
1               5                   10                  15
Phe Val Leu Gly Gly Glu Glu Lys Glu Val Asp Thr Ser Lys Ile Arg
            20                  25                  30

His Val Tyr Arg Tyr Gly Lys His Val Thr Phe Ser Tyr Asp Asp Asn
            35                  40                  45

Gly Lys Leu Gly Leu Gly Leu Val Lys Glu Lys Asp Ala Pro Lys Glu
            50                  55                  60

Leu Leu Asp Met Leu Ala Arg Ala Glu Arg Glu Lys Lys Leu Asn
65                  70                  75
```

<210> SEQ ID NO 3
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 33
<220> FEATURE:
<221> NAME/KEY: DOMAIN
<222> LOCATION: (1)..(12)
<223> OTHER INFORMATION: MRGS-(His)6-tag

<400> SEQUENCE: 3

```
Met Arg Gly Ser His His His His His Gly Ser Val Lys Val Lys
1               5                   10                  15

Phe Thr Trp Tyr Gly Glu Glu Lys Glu Val Asp Thr Ser Lys Ile Met
            20                  25                  30

Ser Val Cys Arg Trp Gly Lys Arg Val Ala Phe Ser Tyr Asp Asp Asn
            35                  40                  45

Gly Lys Ile Asp Tyr Gly Leu Val Asp Glu Lys Asp Ala Pro Lys Glu
            50                  55                  60

Leu Leu Asp Met Leu Ala Arg Ala Glu Arg Glu Lys Lys Leu Asn
65                  70                  75
```

<210> SEQ ID NO 4
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 39
<220> FEATURE:
<221> NAME/KEY: DOMAIN
<222> LOCATION: (1)..(12)
<223> OTHER INFORMATION: MRGS-(His)6-tag

<400> SEQUENCE: 4

```
Met Arg Gly Ser His His His His His Gly Ser Val Lys Val Lys
1               5                   10                  15

Phe Cys Trp Glu Gly Glu Glu Lys Glu Val Asp Thr Ser Lys Ile Arg
            20                  25                  30

His Val Tyr Arg Tyr Gly Lys Tyr Val Thr Phe Ser Tyr Asp Asp Asn
            35                  40                  45

Gly Lys Leu Gly Leu Gly Leu Val Asn Glu Lys Asp Ala Pro Lys Glu
            50                  55                  60

Leu Leu Asp Met Leu Ala Arg Ala Ala
65                  70
```

```
<210> SEQ ID NO 5
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 40
<220> FEATURE:
<221> NAME/KEY: DOMAIN
<222> LOCATION: (1)..(12)
<223> OTHER INFORMATION: MRGS-(His)6-tag

<400> SEQUENCE: 5

Met Arg Gly Ser His His His His His His Gly Ser Val Lys Val Lys
1               5                   10                  15

Phe Gly Glu His Gly Glu Glu Lys Glu Val Asp Thr Ser Lys Ile Met
            20                  25                  30

Ser Val Val Arg Phe Gly Lys Trp Val Cys Phe Arg Tyr Asp Asp Asn
        35                  40                  45

Gly Lys Ala Gly Tyr Gly Ala Val Leu Glu Lys Asp Ala Pro Lys Glu
    50                  55                  60

Leu Leu Asp Met Leu Ala Arg Ala Glu Arg Glu Lys Lys Leu Asn
65                  70                  75

<210> SEQ ID NO 6
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Clone 41
<220> FEATURE:
<221> NAME/KEY: DOMAIN
<222> LOCATION: (1)..(12)
<223> OTHER INFORMATION: MRGS-(His)6-tag

<400> SEQUENCE: 6

Met Arg Gly Ser His His His His His His Gly Ser Val Lys Val Lys
1               5                   10                  15

Phe Val Met Ser Gly Glu Glu Lys Glu Val Asp Thr Ser Lys Ile Met
            20                  25                  30

Ser Val Val Arg Phe Gly Lys Trp Val Cys Phe Arg Tyr Asp Asp Asn
        35                  40                  45

Gly Lys Ala Gly Tyr Gly Ala Val Leu Glu Lys Asp Ala Pro Lys Glu
    50                  55                  60

Leu Leu Asp Met Leu Ala Arg Ala Glu Arg Glu Lys Lys Leu Asn
65                  70                  75

<210> SEQ ID NO 7
<211> LENGTH: 548
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PhoA fusion with clone 6
<220> FEATURE:
<221> NAME/KEY: SIGNAL
<222> LOCATION: (1)..(21)
<223> OTHER INFORMATION: signal peptide
<220> FEATURE:
<221> NAME/KEY: CHAIN
```

```
<222> LOCATION: (29)..(33)
<223> OTHER INFORMATION: linker
<220> FEATURE:
<221> NAME/KEY: BINDING
<222> LOCATION: (34)..(98)
<223> OTHER INFORMATION: PalD-N
<220> FEATURE:
<221> NAME/KEY: CHAIN
<222> LOCATION: (99)..(104)
<223> OTHER INFORMATION: linker
<220> FEATURE:
<221> NAME/KEY: ACT_SITE
<222> LOCATION: (105)..(548)
<223> OTHER INFORMATION: PhoA

<400> SEQUENCE: 7
```

Met Lys Gln Ser Thr Ile Ala Leu Ala Leu Leu Pro Leu Leu Phe Thr
1               5                   10                  15

Pro Val Thr Lys Ala Arg Thr Pro Glu Met Pro Val Asp Gly Thr Gly
            20                  25                  30

Ser Val Lys Val Lys Phe Val Leu Gly Gly Glu Glu Lys Glu Val Asp
        35                  40                  45

Thr Ser Lys Ile Arg His Val Tyr Arg Tyr Gly Lys His Val Thr Phe
    50                  55                  60

Ser Tyr Asp Asp Asn Gly Lys Leu Gly Leu Gly Leu Val Lys Glu Lys
65                  70                  75                  80

Asp Ala Pro Lys Glu Leu Leu Asp Met Leu Ala Arg Ala Glu Arg Glu
                85                  90                  95

Lys Lys Leu Arg Ala Gln Pro Gly Val Leu Glu Asn Arg Ala Ala Gln
            100                 105                 110

Gly Asp Ile Thr Ala Pro Gly Gly Ala Arg Arg Leu Thr Gly Asp Gln
        115                 120                 125

Thr Ala Ala Leu Arg Asp Ser Leu Ser Asp Lys Pro Ala Lys Asn Ile
    130                 135                 140

Ile Leu Leu Ile Gly Asp Gly Met Gly Asp Ser Glu Ile Thr Ala Ala
145                 150                 155                 160

Arg Asn Tyr Ala Glu Gly Ala Gly Gly Phe Phe Lys Gly Ile Asp Ala
                165                 170                 175

Leu Pro Leu Thr Gly Gln Tyr Thr His Tyr Ala Leu Asn Lys Lys Thr
            180                 185                 190

Gly Lys Pro Asp Tyr Val Thr Asp Ser Ala Ala Ser Ala Thr Ala Trp
        195                 200                 205

Ser Thr Gly Val Lys Thr Tyr Asn Gly Ala Leu Gly Val Asp Ile His
    210                 215                 220

Glu Lys Asp His Pro Thr Ile Leu Glu Met Ala Lys Ala Ala Gly Leu
225                 230                 235                 240

Ala Thr Gly Asn Val Ser Thr Ala Glu Leu Gln Gly Ala Thr Pro Ala
                245                 250                 255

Ala Leu Val Ala His Val Thr Ser Arg Lys Cys Tyr Gly Pro Ser Ala
            260                 265                 270

Thr Ser Glu Lys Cys Pro Gly Asn Ala Leu Glu Lys Gly Gly Lys Gly
        275                 280                 285

Ser Ile Thr Glu Gln Leu Leu Asn Ala Arg Ala Asp Val Thr Leu Gly
    290                 295                 300

Gly Gly Ala Lys Thr Phe Ala Glu Thr Ala Thr Ala Gly Glu Trp Gln
305                 310                 315                 320

Gly Lys Thr Leu Arg Glu Gln Ala Gln Ala Arg Gly Tyr Gln Leu Val
                325                 330                 335

```
Ser Asp Ala Ala Ser Leu Asn Ser Val Thr Glu Ala Asn Gln Gln Lys
            340                 345                 350

Pro Leu Leu Gly Leu Phe Ala Asp Gly Asn Met Pro Val Arg Trp Leu
            355                 360                 365

Gly Pro Lys Ala Thr Tyr His Gly Asn Ile Asp Lys Pro Ala Val Thr
370                 375                 380

Cys Thr Pro Asn Pro Gln Arg Asn Asp Ser Val Pro Thr Leu Ala Gln
385                 390                 395                 400

Met Thr Asp Lys Ala Ile Glu Leu Leu Ser Lys Asn Glu Lys Gly Phe
                405                 410                 415

Phe Leu Gln Val Glu Gly Ala Ser Ile Asp Lys Gln Gly His Ala Ala
            420                 425                 430

Asn Pro Cys Gly Gln Ile Gly Glu Thr Val Asp Leu Asp Glu Ala Val
            435                 440                 445

Gln Arg Ala Leu Glu Phe Ala Lys Lys Glu Gly Asn Thr Leu Val Ile
450                 455                 460

Val Thr Ala Asp His Ala His Ala Ser Gln Ile Val Ala Pro Asp Thr
465                 470                 475                 480

Lys Ala Pro Gly Leu Thr Gln Ala Leu Asn Thr Lys Asp Gly Ala Val
                485                 490                 495

Met Val Met Ser Tyr Gly Asn Ser Glu Glu Asp Ser Gln Glu His Thr
            500                 505                 510

Gly Ser Gln Leu Arg Ile Ala Ala Tyr Gly Pro His Ala Ala Asn Val
            515                 520                 525

Val Gly Leu Thr Asp Gln Thr Asp Leu Phe Tyr Thr Met Lys Ala Ala
            530                 535                 540

Leu Gly Leu Lys
545

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GFP fusion with clone 6
<220> FEATURE:
<221> NAME/KEY: BINDING
<222> LOCATION: (13)..(77)
<223> OTHER INFORMATION: PalD-N
<220> FEATURE:
<221> NAME/KEY: CHAIN
<222> LOCATION: (78)..(87)
<223> OTHER INFORMATION: linker
<220> FEATURE:
<221> NAME/KEY: ACT_SITE
<222> LOCATION: (88)..(329)
<223> OTHER INFORMATION: GFP

<400> SEQUENCE: 8

Met Arg Gly Ser His His His His His His Gly Ser Val Lys Val Lys
1               5                   10                  15

Phe Val Leu Gly Gly Glu Glu Lys Glu Val Asp Thr Ser Lys Ile Arg
            20                  25                  30

His Val Tyr Arg Tyr Gly Lys His Val Thr Phe Ser Tyr Asp Asp Asn
        35                  40                  45

Gly Lys Leu Gly Leu Gly Leu Val Lys Glu Lys Asp Ala Pro Lys Glu
    50                  55                  60
```

Leu Leu Asp Met Leu Ala Arg Ala Glu Arg Glu Lys Leu Gly Ser
 65                  70                  75                  80

Ala Gly Ser Ala Ala Gly Ser Gly Glu Phe Ser Lys Gly Glu Glu Leu
                 85                  90                  95

Phe Thr Gly Val Val Pro Ile Leu Val Glu Leu Asp Gly Asp Val Asn
            100                 105                 110

Gly His Lys Phe Ser Val Ser Gly Glu Gly Glu Gly Asp Ala Thr Tyr
        115                 120                 125

Gly Lys Leu Thr Leu Lys Phe Ile Cys Thr Thr Gly Lys Leu Pro Val
    130                 135                 140

Pro Trp Pro Thr Leu Val Thr Thr Leu Thr Tyr Gly Val Gln Cys Phe
145                 150                 155                 160

Ser Arg Tyr Pro Asp His Met Lys Arg His Asp Phe Phe Lys Ser Ala
                165                 170                 175

Met Pro Glu Gly Tyr Val Gln Glu Arg Thr Ile Ser Phe Lys Asp Asp
            180                 185                 190

Gly Asn Tyr Lys Thr Arg Ala Glu Val Lys Phe Glu Gly Asp Thr Leu
        195                 200                 205

Val Asn Arg Ile Glu Leu Lys Gly Ile Asp Phe Lys Glu Asp Gly Asn
    210                 215                 220

Ile Leu Gly His Lys Leu Glu Tyr Asn Tyr Asn Ser His Asn Val Tyr
225                 230                 235                 240

Ile Thr Ala Asp Lys Gln Lys Asn Gly Ile Lys Ala Asn Phe Lys Ile
                245                 250                 255

Arg His Asn Ile Glu Asp Gly Ser Val Gln Leu Ala Asp His Tyr Gln
            260                 265                 270

Gln Asn Thr Pro Ile Gly Asp Gly Pro Val Leu Leu Pro Asp Asn His
        275                 280                 285

Tyr Leu Ser Thr Gln Ser Ala Leu Ser Lys Asp Pro Asn Glu Lys Arg
    290                 295                 300

Asp His Met Val Leu Leu Glu Phe Val Thr Ala Ala Gly Ile Thr His
305                 310                 315                 320

Gly Met Asp Glu Leu Tyr Lys Thr Gly Asn
                325                 330

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaactccta ggtattgtgc tgacgacccc gatcgcgatc tctagctttg cggtgaaagt    60
gaaatt                                                              66

<210> SEQ ID NO 10
<211> LENGTH: 68
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gatcttgctg gtgtccactt cttttcttc gcctttatat ttaaatttca ctttcaccgc    60
aaagctag                                                                68

<210> SEQ ID NO 11
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaagtggaca ccagcaagat caagaaagtt tggcgtgtgg gcaaaatggt gagctttacc    60
tacgacgaca acggcaag                                                  78

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctctttcggg gcatctttct cgctcacggc gccacggccg gtcttgccgt tgtcgtcgta    60

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagaaagatg ccccgaaaga gttattagat atgttagcgc gtgcggaaag cttcaacca     59

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tggtggttga agctttccgc acg                                            23

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
attaatggta ccggatccgt gaaagtgaaa tttaaatata aag                      43

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataattgagc tctaagcttt ttttcacgtt ccgcacgcgc taacatatc    49

<210> SEQ ID NO 17
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atacgaaatt aatacgactc actataggga gaccacaacg gtttccctc    49

<210> SEQ ID NO 18
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agaccacaac ggtttccctc tagaaataat tttgtttaac tttaagaagg agatatatcc    60
atgagaggat cg    72

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggagatatat ccatgagagg atcgcatcac catcaccatc acggatccgt caaggtgaaa    60
ttc    63

<210> SEQ ID NO 20
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: misc_feature
<222> LOCATION: (28)..(29)
<223> OTHER INFORMATION: n is a, c, g, or t

<400> SEQUENCE: 20
ggatccgtca aggtgaaatt cnnsnnsnns ggcgaagaaa aagaagtgga cactagtaag    60
atc    63

<210> SEQ ID NO 21
<211> LENGTH: 78
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: misc_feature
<222> LOCATION: (56)..(57)
<223> OTHER INFORMATION: n is a, c, g, or t

<400> SEQUENCE: 21
cttgccgttg tcgtcgtasn naaasnncac snntttgccs nnacgsnnaa csnnsnngat    60
cttactagtg tccacttc    78

```
<210> SEQ ID NO 22
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t

<400> SEQUENCE: 22
taataactct ttcggggcat ctttctcsnn cacsnngccs nngccsnnct tgccgttgtc      60
gtcgta                                                                66

<210> SEQ ID NO 23
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccatataaag cttttctctcg cgttccgcac gcgctaacat atctaataac tctttcgggg    60
catc                                                                  64

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcggaacgcg agaaaaagct ttatatggcc tcgggggcc                            39

<210> SEQ ID NO 25
<211> LENGTH: 45
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 25
ccgcacacca gtaaggtgtg cggtttcagt tgccgctttc tttct                    45

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
attaatggta ccggatccgt gaaggtgaaa ttc                                 33

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ataattgagc tctaagcttt ttttcacgct ccgcac                              36

<210> SEQ ID NO 28
<211> LENGTH: 64
<212> TYPE: PRT
<213> ORGANISM: Sulfolobus sp.

<400> SEQUENCE: 28

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 29
<211> LENGTH: 89
<212> TYPE: PRT
<213> ORGANISM: Escherichia coli

<400> SEQUENCE: 29

Met Lys Lys Met Phe Met Ala Val Leu Phe Ala Leu Val Ser Val Asn
1               5                   10                  15

Ala Met Ala Ala Asp Cys Ala Lys Gly Lys Ile Glu Phe Ser Lys Tyr
            20                  25                  30

Asn Glu Asp Asp Thr Phe Thr Val Lys Val Asp Gly Lys Glu Tyr Trp
        35                  40                  45

Thr Ser Arg Trp Asn Leu Gln Pro Leu Leu Gln Ser Ala Gln Leu Thr
    50                  55                  60

Gly Met Thr Val Thr Ile Lys Ser Ser Thr Cys Glu Ser Gly Ser Gly
65                  70                  75                  80

Phe Ala Glu Val Gln Phe Asn Asn Asp
                85
```

<210> SEQ ID NO 30
<211> LENGTH: 128
<212> TYPE: PRT
<213> ORGANISM: Homo sapiens

<400> SEQUENCE: 30

Met Ser Leu Arg Leu Asp Thr Thr Pro Ser Cys Asn Ser Ala Arg Pro
1               5                   10                  15

Leu His Ala Leu Gln Val Leu Leu Leu Ser Leu Leu Leu Thr Ala
            20                  25                  30

Leu Ala Ser Ser Thr Lys Gly Gln Thr Lys Arg Asn Leu Ala Lys Gly
        35                  40                  45

Lys Glu Glu Ser Leu Asp Ser Asp Leu Tyr Ala Glu Leu Arg Cys Met
    50                  55                  60

Cys Ile Lys Thr Thr Ser Gly Ile His Pro Lys Asn Ile Gln Ser Leu
65                  70                  75                  80

Glu Val Ile Gly Lys Gly Thr His Cys Asn Gln Val Glu Val Ile Ala
                85                  90                  95

Thr Leu Lys Asp Gly Arg Lys Ile Cys Leu Asp Pro Asp Ala Pro Arg
            100                 105                 110

Ile Lys Lys Ile Val Gln Lys Lys Leu Ala Gly Asp Glu Ser Ala Asp
        115                 120                 125

<210> SEQ ID NO 31
<211> LENGTH: 142
<212> TYPE: PRT
<213> ORGANISM: Azotobacter vinelandii

<400> SEQUENCE: 31

Met Lys Ile Ser Ala Arg Asn Val Phe Lys Gly Thr Val Ser Ala Leu
1               5                   10                  15

Lys Glu Gly Ala Val Asn Ala Glu Val Asp Ile Leu Gly Gly Gly
            20                  25                  30

Asp Lys Leu Ala Ala Val Val Thr Leu Glu Ser Ala Arg Ser Leu Gln
        35                  40                  45

Leu Ala Ala Gly Lys Glu Val Val Ala Val Lys Ala Pro Trp Val
    50                  55                  60

Leu Leu Met Thr Asp Ser Ser Gly Tyr Arg Leu Ser Ala Arg Asn Ile
65                  70                  75                  80

Leu Thr Gly Thr Val Lys Thr Ile Glu Thr Gly Ala Val Asn Ala Glu
                85                  90                  95

Val Thr Leu Ala Leu Gln Gly Gly Thr Glu Ile Thr Ser Met Val Thr
            100                 105                 110

Lys Glu Ala Val Ala Glu Leu Gly Leu Lys Pro Gly Ala Ser Ala Ser
        115                 120                 125

Ala Val Ile Lys Ala Ser Asn Val Ile Leu Gly Val Pro Ala
    130                 135                 140

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Lys Leu Gly Ser Ala Gly Ser Ala Ala Gly Ser Gly Glu Phe
1               5                   10
```

<210> SEQ ID NO 33
<211> LENGTH: 65
<212> TYPE: PRT
<213> ORGANISM: Sulfolobus sp.

<400> SEQUENCE: 33

```
Val Lys Val Lys Phe Lys Tyr Lys Gly Glu Glu Lys Glu Val Asp Thr
1               5                   10                  15

Ser Lys Ile Lys Lys Val Trp Arg Val Gly Lys Met Val Ser Phe Thr
                20                  25                  30

Tyr Asp Asp Asn Gly Lys Thr Gly Arg Gly Ala Val Ser Glu Lys Asp
            35                  40                  45

Ala Pro Lys Glu Leu Leu Asp Met Leu Ala Arg Ala Glu Arg Glu Lys
    50                  55                  60

Lys
65
```

<210> SEQ ID NO 34
<211> LENGTH: 63
<212> TYPE: PRT
<213> ORGANISM: Sulfolobus acidocaldarius

<400> SEQUENCE: 34

```
Lys Val Arg Phe Lys Tyr Lys Gly Glu Glu Lys Glu Val Asp Thr Ser
1               5                   10                  15

Lys Ile Lys Lys Val Trp Arg Val Gly Lys Met Val Ser Phe Thr Tyr
                20                  25                  30

Asp Asp Asn Gly Lys Thr Gly Arg Gly Ala Val Ser Glu Lys Asp Ala
            35                  40                  45

Pro Lys Glu Leu Met Asp Met Leu Ala Arg Ala Glu Lys Lys Lys
    50                  55                  60
```

<210> SEQ ID NO 35
<211> LENGTH: 63
<212> TYPE: PRT
<213> ORGANISM: Sulfolobus tokodaii

<400> SEQUENCE: 35

```
Val Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
                20                  25                  30

Tyr Asp Asp Asn Gly Lys Thr Gly Arg Gly Ala Val Ser Glu Lys Asp
            35                  40                  45

Ala Pro Lys Glu Leu Leu Gln Met Leu Glu Lys Ser Gly Lys Lys
    50                  55                  60
```

<210> SEQ ID NO 36
<211> LENGTH: 62
<212> TYPE: PRT
<213> ORGANISM: Sulfolobus shibatae

<400> SEQUENCE: 36

```
Val Thr Val Lys Phe Lys Tyr Lys Gly Glu Glu Lys Glu Val Asp Thr
1               5                   10                  15

Ser Lys Ile Lys Lys Val Trp Arg Val Gly Lys Met Ile Ser Phe Thr
                20                  25                  30
```

Tyr Asp Glu Gly Gly Lys Thr Gly Arg Gly Ala Val Ser Glu Lys Asp
          35                  40                  45

Ala Pro Lys Glu Leu Leu Gln Met Leu Glu Lys Gln Lys Lys
 50                  55                  60

<210> SEQ ID NO 37
<211> LENGTH: 60
<212> TYPE: PRT
<213> ORGANISM: Sulfolobus solfataricus

<400> SEQUENCE: 37

Val Lys Phe Lys Tyr Lys Gly Glu Glu Lys Glu Val Asp Ile Ser Lys
  1               5                  10                  15

Ile Lys Lys Val Trp Arg Val Gly Lys Met Ile Ser Phe Thr Tyr Asp
             20                  25                  30

Glu Gly Gly Lys Thr Gly Arg Gly Ala Val Ser Glu Lys Asp Ala Pro
         35                  40                  45

Lys Glu Leu Leu Gln Met Leu Glu Lys Gln Lys Lys
 50                  55                  60

<210> SEQ ID NO 38
<211> LENGTH: 60
<212> TYPE: PRT
<213> ORGANISM: Sulfolobus shibatae

<400> SEQUENCE: 38

Val Lys Phe Lys Tyr Lys Gly Glu Glu Lys Gln Val Asp Ile Ser Lys
  1               5                  10                  15

Ile Lys Lys Val Trp Arg Val Gly Lys Met Ile Ser Phe Thr Tyr Asp
             20                  25                  30

Glu Gly Gly Lys Thr Gly Arg Gly Ala Val Ser Glu Lys Asp Ala Pro
         35                  40                  45

Lys Glu Leu Leu Gln Met Leu Glu Lys Gln Lys Lys
 50                  55                  60

<210> SEQ ID NO 39
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Val Lys Val Lys Phe Val Leu Gly Gly Glu Glu Lys Glu Val Asp Thr
  1               5                  10                  15

Ser Lys Ile Arg His Val Tyr Arg Tyr Gly Lys His Val Thr Phe Ser
             20                  25                  30

Tyr Asp Asp Asn Gly Lys Leu Gly Leu Gly Leu Val Lys Glu Lys Asp
         35                  40                  45

Ala Pro Lys Glu Leu Leu Asp Met Leu Ala Arg Ala Glu Arg Glu Lys
 50                  55                  60

Lys
 65

<210> SEQ ID NO 40
<211> LENGTH: 65
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 40

Val Lys Val Lys Phe Trp Gly Ser Gly Glu Glu Lys Glu Val Asp Thr
1               5                   10                  15

Ser Lys Ile Arg Ser Val Gly Arg Met Gly Lys Leu Val Ala Phe Arg
            20                  25                  30

Tyr Asp Asp Asn Gly Lys Asn Gly Tyr Gly Val Val Asp Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 41
<211> LENGTH: 65
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Val Lys Val Lys Phe Thr Val Leu Gly Glu Glu Lys Glu Val Asp Thr
1               5                   10                  15

Ser Lys Ile Leu Arg Val Ala Arg Tyr Gly Lys Ala Val Cys Phe Arg
            20                  25                  30

Tyr Asp Asp Asn Gly Lys Ile Gly Tyr Gly Leu Val Ile Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 42
<211> LENGTH: 65
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Val Lys Val Lys Phe Thr Trp Tyr Gly Glu Glu Lys Glu Val Asp Thr
1               5                   10                  15

Ser Lys Ile Met Ser Val Cys Arg Trp Gly Lys Arg Val Ala Phe Ser
            20                  25                  30

Tyr Asp Asp Asn Gly Lys Ile Asp Tyr Gly Leu Val Asp Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 43
<211> LENGTH: 61
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 43

Val Lys Val Lys Phe Cys Trp Glu Gly Glu Glu Lys Glu Val Asp Thr
1               5                   10                  15

Ser Lys Ile Arg His Val Tyr Arg Tyr Gly Lys Tyr Val Thr Phe Ser
            20                  25                  30

Tyr Asp Asp Asn Gly Lys Leu Gly Leu Gly Leu Val Asn Glu Lys Asp
        35                  40                  45

Ala Pro Lys Glu Leu Leu Asp Met Leu Ala Arg Ala Ala
    50                  55                  60

<210> SEQ ID NO 44
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Lys Val Lys Phe Gly Glu His Gly Glu Glu Lys Glu Val Asp Thr
1               5                   10                  15

Ser Lys Ile Met Ser Val Val Arg Phe Gly Lys Trp Val Cys Phe Arg
            20                  25                  30

Tyr Asp Asp Asn Gly Lys Ala Gly Tyr Gly Ala Val Leu Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 45
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Val Lys Val Lys Phe Val Met Ser Gly Glu Lys Glu Val Asp Thr
1               5                   10                  15

Ser Lys Ile Met Ser Val Val Arg Phe Gly Lys Trp Val Cys Phe Arg
            20                  25                  30

Tyr Asp Asp Asn Gly Lys Ala Gly Tyr Gly Ala Val Leu Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 46
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Val Lys Val Lys Phe Glu Ile Ser Gly Glu Glu Lys Glu Val Asp Thr
1               5                   10                  15

Ser Lys Ile Ser Ser Val Ala Arg Leu Gly Lys Leu Val Ala Phe Arg
            20                  25                  30

Tyr Asp Asp Asn Gly Lys Thr Gly Tyr Gly Val Val Pro Glu Lys Asp
        35                  40                  45

Ala Pro Lys Glu Leu Leu Asp Met Leu Ala Arg Ala Glu Arg Glu Lys
    50                  55                  60

Lys
65

<210> SEQ ID NO 47
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Ser Val Lys Val Lys Phe Leu Tyr Leu Gly Glu Glu Lys Glu Val
1               5                   10                  15

Asp Thr Ser Lys Ile Trp Phe Val Met Arg Ala Gly Lys His Val Tyr
            20                  25                  30

Phe Gln Tyr Asp Asp Asn Gly Lys Tyr Gly Ile Gly Trp Val Arg Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atacgaaatt aatacgactc actataggga gaccacaacg g                        41

<210> SEQ ID NO 49
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(10)
<223> OTHER INFORMATION: Any amino acid
<220> FEATURE:
<221> NAME/KEY: MOD_RES
<222> LOCATION: (22)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
```

```
<221> NAME/KEY: MOD_RES
<222> LOCATION: (30)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (45)..(45)
<223> OTHER INFORMATION: Any amino acid
<220> FEATURE:
<221> NAME/KEY: MOD_RES
<222> LOCATION: (47)..(47)
<223> OTHER INFORMATION: Any amino acid

<400> SEQUENCE: 49

Gly Ser Val Lys Val Lys Phe Xaa Xaa Xaa Gly Glu Glu Lys Glu Val
1               5                   10                  15

Asp Thr Ser Lys Ile Xaa Xaa Val Xaa Arg Xaa Gly Lys Xaa Val Xaa
                20                  25                  30

Phe Xaa Tyr Asp Asp Asn Gly Lys Xaa Gly Xaa Gly Xaa Val Xaa Glu
            35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 50
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Ser Val Lys Val Lys Phe Gly Val Asp Gly Glu Glu Lys Glu Val
1               5                   10                  15

Asp Thr Ser Lys Ile Val Trp Val Lys Arg Ala Gly Lys Cys Val Leu
                20                  25                  30

Phe Ile Tyr Asp Asp Asn Gly Lys Asn Gly Tyr Gly Asp Val Thr Glu
            35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 51
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 52
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 53
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 54
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 55
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 56
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 57
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gly Ser Val Lys Val Lys Phe Ile Val Met Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 58
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gly Ser Val Lys Val Lys Phe Ile Val Met Asp Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 59
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gly Ser Val Lys Val Lys Phe Phe Trp Asn Gly Glu Glu Lys Glu Val
1               5                   10                  15

Asp Thr Ser Lys Ile Val Trp Val Lys Arg Ala Gly Lys Cys Val Leu
            20                  25                  30

Phe Ile Tyr Asp Asp Asn Gly Lys Asn Gly Tyr Gly Asp Val Thr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 60
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Gly Ser Val Lys Val Lys Phe Val Met Cys Gly Glu Glu Lys Glu Val
1               5                   10                  15

Asp Thr Ser Lys Ile Ile Thr Val Lys Arg Thr Gly Lys Glu Val Asp
            20                  25                  30

Phe Leu Tyr Asp Asp Asn Gly Lys Asn Gly Tyr Gly Thr Val Tyr Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 61
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Ser Val Lys Val Lys Phe Asp Leu Cys Gly Glu Glu Lys Glu Val
1               5                   10                  15

Asp Thr Ser Lys Ile Val Tyr Val Ala Arg Asp Gly Lys Thr Val Leu
            20                  25                  30

Phe Met Tyr Asp Asp Asn Gly Lys Ser Gly Arg Gly Val Ser Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 62
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gly Ser Val Lys Val Lys Phe Lys Tyr Lys Gly Glu Glu Lys Glu Val
1               5                   10                  15

Asp Thr Ser Lys Ile Lys Val Trp Arg Val Gly Lys Met Val Ser
            20                  25                  30

Phe Thr Tyr Asp Asp Asn Gly Lys Thr Gly Arg Gly Ala Val Ser Glu
        35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 63
<211> LENGTH: 68
<212> TYPE: PRT
<213> ORGANISM: Artificial Sequence
<220> FEATURE:
<223> OTHER INFORMATION: Description of Artificial Sequence: Synthetic
      Consensus sequence

<400> SEQUENCE: 63

Gly Ser Val Lys Val Lys Phe Leu Tyr Leu Gly Glu Glu Lys Glu Val
```

```
                1               5                   10                  15
Asp Thr Ser Lys Ile Lys Lys Val Met Arg Ala Gly Lys His Val Ser
                20                  25                  30

Phe Gln Tyr Asp Asp Asn Gly Lys Thr Gly Arg Gly Ala Val Arg Glu
            35                  40                  45

Lys Asp Ala Pro Lys Glu Leu Leu Asp Met Leu Ala Arg Ala Glu Arg
    50                  55                  60

Glu Lys Lys Leu
65

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Gly Ser His His His His His His
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 65

His His His His His His
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Arg Gly Ser His His His His His His
1               5                   10

<210> SEQ ID NO 67
<211> LENGTH: 64
<212> TYPE: PRT
<213> ORGANISM: Sulfolobus solfataricus

<400> SEQUENCE: 67

Met Ala Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
    50                  55                  60
```